United States Patent
Puttananjegowda et al.

(10) Patent No.: US 11,764,735 B2
(45) Date of Patent: Sep. 19, 2023

(54) CASCODE COMMON SOURCE TRANSIMPEDANCE AMPLIFIERS FOR ANALYTE MONITORING SYSTEMS

(71) Applicant: UNIVERSITY OF SOUTH FLORIDA, Tampa, FL (US)

(72) Inventors: Kavyashree Puttananjegowda, Tampa, FL (US); Sylvia Thomas, Orlando, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/696,648

(22) Filed: Mar. 16, 2022

(65) Prior Publication Data
US 2022/0263476 A1  Aug. 18, 2022

Related U.S. Application Data

(63) Continuation of application No. 16/008,864, filed on Jun. 14, 2018, now Pat. No. 11,309,846.
(Continued)

(51) Int. Cl.
*H03F 1/22* (2006.01)
*G01N 27/327* (2006.01)
(Continued)

(52) U.S. Cl.
CPC ............ *H03F 1/223* (2013.01); *G01N 27/327* (2013.01); *H03F 3/16* (2013.01); *H03F 3/345* (2013.01);
(Continued)

(58) Field of Classification Search
CPC . H03F 1/223; H03F 3/16; H03F 3/345; H03F 2200/129; H03F 2200/144;
(Continued)

(56) References Cited

U.S. PATENT DOCUMENTS 6,690,239 B2  2/2004 Wilson
7,239,905 B2  7/2007 Kiani-Azarbayjany et al.
(Continued)

OTHER PUBLICATIONS

Amlani et al., "Measuring frequency response of a single-walled carbon nanotube common-source amplifier", IEEE Transactions on Nanotechnology, vol. 8, pp. 226-223 (2009).
(Continued)

*Primary Examiner* — Khanh V Nguyen
(74) *Attorney, Agent, or Firm* — QUARLES & BRADY LLP

(57) ABSTRACT

A biosensor for an analyte monitoring system. In one embodiment, the biosensor includes a cascode common source transimpedance amplifier circuit, an analog to digital converter, and an output circuit. The cascode common source transimpedance amplifier circuit is configured to receive an electrical current generated by an electrochemical reaction of an analyte on a test strip. The cascode common source transimpedance amplifier circuit is also configured to convert the electrical current to an analog voltage signal. The analog to digital converter is configured to convert the analog voltage signal to a digital voltage signal. The output circuit is configured to transmit a signal indicating a measured level of the analyte based on the digital voltage signal.

17 Claims, 12 Drawing Sheets

Related U.S. Application Data

(60) Provisional application No. 62/550,189, filed on Aug. 25, 2017.

(51) Int. Cl.
  *H03F 3/16* (2006.01)
  *H03F 3/345* (2006.01)
  *H10K 19/10* (2023.01)

(52) U.S. Cl.
  CPC ...... *H10K 19/10* (2023.02); *B01L 2300/0636* (2013.01); *B01L 2300/0825* (2013.01); *H03F 2200/129* (2013.01); *H03F 2200/144* (2013.01); *H03F 2200/294* (2013.01)

(58) Field of Classification Search
  CPC ............ H03F 2200/294; G01N 27/327; G01N 33/49; H01L 27/283; H01L 51/0048; H01L 51/0541; B01L 2300/0636; B01L 2300/0825; B01L 2300/023; B01L 3/5023
  USPC ................................................ 330/277, 311
  See application file for complete search history.

(56) References Cited

U.S. PATENT DOCUMENTS

| | | |
|---|---|---|
| 7,768,387 B2 | 8/2010 | Fennell |
| 7,944,290 B2 | 5/2011 | Yeung |
| 3,029,460 A1 | 10/2011 | Rush et al. |
| 8,427,298 B2 * | 4/2013 | Fennell ................ A61B 5/7475 205/792 |
| 8,466,741 B2 | 6/2013 | Umeda |
| 8,513,741 B2 | 8/2013 | Keshavarzi |
| 9,121,050 B2 | 9/2015 | Franciskovich |
| 9,509,400 B2 | 11/2016 | Jain |
| 9,880,126 B2 | 1/2018 | Kim |
| 10,249,741 B2 | 4/2019 | Smith |
| 2011/0120871 A1 | 5/2011 | Reid |
| 2012/0049890 A1 | 3/2012 | Keshavarzi et al. |
| 2012/0301360 A1 | 11/2012 | Meinhold |
| 2016/0206232 A1 | 7/2016 | Bordelon |

OTHER PUBLICATIONS

Dalvi, "AN1560—Glucose Meter Reference Design," brochure (2013) Microchip Technology Inc., pp. 1-20.

Deng et al., "A Compact SPICE model for carbon-nanotube field-effect transistors including non-idealities and its application Part I: Model of the intrinsic channel region," IEEE Trans. Electron. Devices, vol. 54, No. 12, pp. 3186-3194 (2007).

Diaa, "Low Power Transimpedance Amplifier Using Current Reuse with Dual Feedback", IEEE International Conference on Electronics, Circuits and Systems, pp. 244-247 (2015).

Ferrari et al., "A current-sensitive front-end amplifier for nano-biosensors with a 2MHz BW," ISSCC Dig. Tech. Papers, pp. 164-165 (2007).

Guo et al., "Assessment of High-Frequency Performance Potential of Carbon Nanotube Transistors" IEEE Transactions on Nanotechnology, vol. 4, No. 6, pp. 715-721 (2005).

Hu et al., "A Low-Power 100MO CMOS Front-end Transimpedance Amplifier for Biosensing Applications," IEEE International Midwest Symposium on Circuits and Systems, pp. 541-544 (2010).

Javey et al., "Self-aligned ballistic molecular transistors and electrically parallel nanotube arrays", Nano Letters, vol. 4, pp. 1319-1322(2004).

Javey et al., "Ballistic carbon nanotube field-effect transistors", Nature, vol. 424, pp. 654-657 (2003).

Kamat et al., "Blood Glucose Measurement Using Bioimpedance Technique," Advances in Electronics, vol. Article ID 406257, 5 pages, (2014).

Kansu, "A Transimpedance Amplifier for Capacitive Micromachined Ultrasonic Transducers," Master's Thesis Desertion (2015).

Landauer et al., "Carbon Nanolube FET Process Variability and Noise Model for Radio frequency Investigations", EEE International Conference on Nanotechnology, vol. 1, pp. 1-5 (2012).

Lee et al., "Low Power CMOS Adaptive Electronic Central Pattern Generator Design for a Biomimelic Robot," Neurocomputing, vol. 71, pp. 284-296 (2007).

McEuen et al., "Single-walled carbon nanolube electronics", IEEE Transactions on Nanotechnology, vol. 1, No. 1, pp. 78-85 (2002).

Ponchet et al., "A Design Methodology for Low-Noise CMOS Transimpedance Amplifiers Based on Shunt-Shunt Feedback Topology," IEEE Symposium on Integrated Circuits and System Design, 1-6 (2016).

Puttananjegowda et al., "An Ultra-Low-Power Multi-Stage Transimpedance Amplifier using Carbon Nanolube FETs for Biosensing Applications," Manuscript presented at 2018 IEEE 9th Annual Information Technology, Electronics and Mobile Communication Conference (IEMCON), 2018, 6 pages.

Puttananjegowda et al., "The Design of Ultra Low Noise Transimpedance Amplifier for Blood Glucose Monitoring Systems," 2017 IEEE 8th Annual Ubiquitous Computing, Electronics and Mobile Communication Conference UEMCON), 2017, 5 pages.

Raychowdhury et al., "Carbon-nanolube-based voltage-mode multiple-valued logic design", IEEE Transactions on Nanotechnology, vol. 4, No. 2, pp. 168-179 (2005).

Sharma et al., "A 104-dB dynamic range transimpedance-based CMOS ASIC for tuning fork microgyroscopes," IEEE Solid-Slate Circuits, vol. 42, pp. 1790-1802 (2007).

Stanford University CNFET Model website [Online], Available: http://nano.stanford.edu/model.php (2015).

Texas Instruments, "Microconlrollers in Blood Glucose Meiers," brochure (2015) 3 pages.

Yang et al., "Amperomelric electrochemical microsystem for a miniaturized protein biosensor array," IEEE Trans. Biomed Circuits Syst., vol. 3, No. 3, pp. 160-168 (2009).

* cited by examiner

PRIOR ART

CASCODE COMMON SOURCE TRANSIMPEDANCE AMPLIFIERS FOR ANALYTE MONITORING SYSTEMS

RELATED APPLICATIONS

This application is a continuation of U.S. patent application Ser. No. 16/008,864, filed Jun. 14, 2018, which claims the benefit of priority of U.S. Provisional Application No. 62/550,189, entitled "ULTRA LOW NOISE TRANSIMPEDANCE AMPLIFIER FOR BLOOD GLUCOSE MONITORING SYSTEMS," filed Aug. 25, 2017, all of which are herein incorporated by reference in full.

FIELD

The disclosure relates to analyte monitoring methods and systems.

SUMMARY

With the recent advancements in the bioelectronics field, low cost, low power, and ease of miniaturization have made electronic biosensors a promising candidate for point-of-care diagnostics and detection. In literature, biosensors have been reported for monitoring blood glucose levels in diabetic patients. Diabetes is a disorder associated with an insufficiency of insulin secretion. A large number of people around the world suffer from this disorder, which can result in damage to eyes, kidneys, nerves, and even death. A common method to detect diabetes is to monitor the levels of glucose in the blood stream using biosensors. The fundamental idea behind the development of these biosensors is to have a glucose monitoring system which is portable. In addition, these biosensors require very high sensitivity readout circuitry because of their small size and low power requirements. Biosensor output currents range from picoamps to nanoamps for low frequencies (for example, frequencies between 1 hertz to 50 kilohertz). Accordingly, highly sensitive and selective current measuring circuitry is required.

Thus, the disclosure provides a biosensor for an analyte monitoring system. In one embodiment, the biosensor includes a cascode common source transimpedance amplifier circuit, an analog to digital converter, and an output circuit. The cascode common source transimpedance amplifier circuit is configured to receive an electrical current generated by an electrochemical reaction of an analyte on a test strip. The cascode common source transimpedance amplifier circuit is also configured to convert the electrical current to an analog voltage signal. The analog to digital converter is configured to convert the analog voltage signal to a digital voltage signal. The output circuit is configured to transmit a signal indicating a measured level of the analyte based on the digital voltage signal.

The disclosure also provides a cascode common source transimpedance amplifier circuit implemented in a 180 nanometer complementary metal oxide semiconductor (CMOS) process. The CMOS-based cascode common source transimpedance amplifier circuit is suitable for low noise and low power front end amplification stage in integrated biosensing applications. The CMOS-based cascode common source transimpedance amplifier circuit exhibits low input impedance, low input-referred noise current, low power consumption, low noise, high transimpedance gain, low cost, and is capable of detecting low frequency signals. The CMOS-based cascode common source transimpedance amplifier circuit consumes 45.7 microwatts from a 1.4 volt voltage supply. The CMOS-based cascode common source transimpedance amplifier circuit has a high transimpedance gain of 1.72 gigaohms with a bandwidth of 180 kilohertz and a low input-referred noise current of 22.4 fA/√hertz.

The disclosure further provides a cascode common source transimpedance amplifier circuit implemented in a 32 nanometer carbon nanotube technology. The carbon nanotube-based cascode common source transimpedance amplifier circuit is suitable for low noise and low power front end amplification stage in integrated biosensing applications. The carbon nanotube-based cascode common source transimpedance amplifier circuit may exhibit low-noise power consumption, low input impedance, and high transimpedance gain. The carbon nanotube-based cascode common source transimpedance amplifier circuit consumes approximately 6.3 picowatts from an approximately 1.8 volt supply. The carbon nanotube-based cascode common source transimpedance amplifier circuit has a high transimpedance gain of 5.7 gigaohms with a bandwidth of 200 megahertz and a low input-referred noise current of 4.3 fA/√hertz.

Other aspects of the disclosure will become apparent by consideration of the detailed description and accompanying drawings.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

The phrase "series-type configuration" as used herein refers to a circuit arrangement in which the described elements are arranged, in general, in a sequential fashion such that the output of one element is coupled to the input of another, though the same current may not pass through each element. For example, in a "series-type configuration," additional circuit elements may be connected in parallel with one or more of the elements in the "series-type configuration." Furthermore, additional circuit elements can be connected at nodes in the series-type configuration such that branches in the circuit are present. Therefore, elements in a series-type configuration do not necessarily form a true "series circuit."

Additionally, the phrase "parallel-type configuration" as used herein refers to a circuit arrangement in which the described elements are arranged, in general, in a manner such that one element is connected to another element, such that the circuit forms a parallel branch of the circuit arrangement. In such a configuration, the individual elements of the circuit may not have the same potential difference across them individually. For example, in a parallel-type configuration of the circuit, two circuit elements in parallel with one another may be connected in series with one or more additional elements of the circuit. Therefore, a circuit in a "parallel-type configuration" can include elements that do not necessarily individually form a true "parallel circuit."

Additionally, the phrase "cascode connected" as used herein refers to a circuit arrangement in which the described elements are arranged, in general, in a sequential fashion such that the drain (or collector) of a first element is coupled to the source (or emitter) of a second element, such that the first element operates as a common source (or common emitter) stage feeding into the second element which operates as a common gate (or common base) stage. In such a configuration, the same current may not pass through each of the "cascode connected" elements. For example, additional circuit elements may be connected in parallel with one or more of the "cascode connected" elements. Furthermore, additional circuit elements can be connected at nodes of the "cascode connected" elements such that branches in the circuit are present. Therefore, "cascode connected" elements do not necessarily form a true "cascode circuit."

Figure 1:
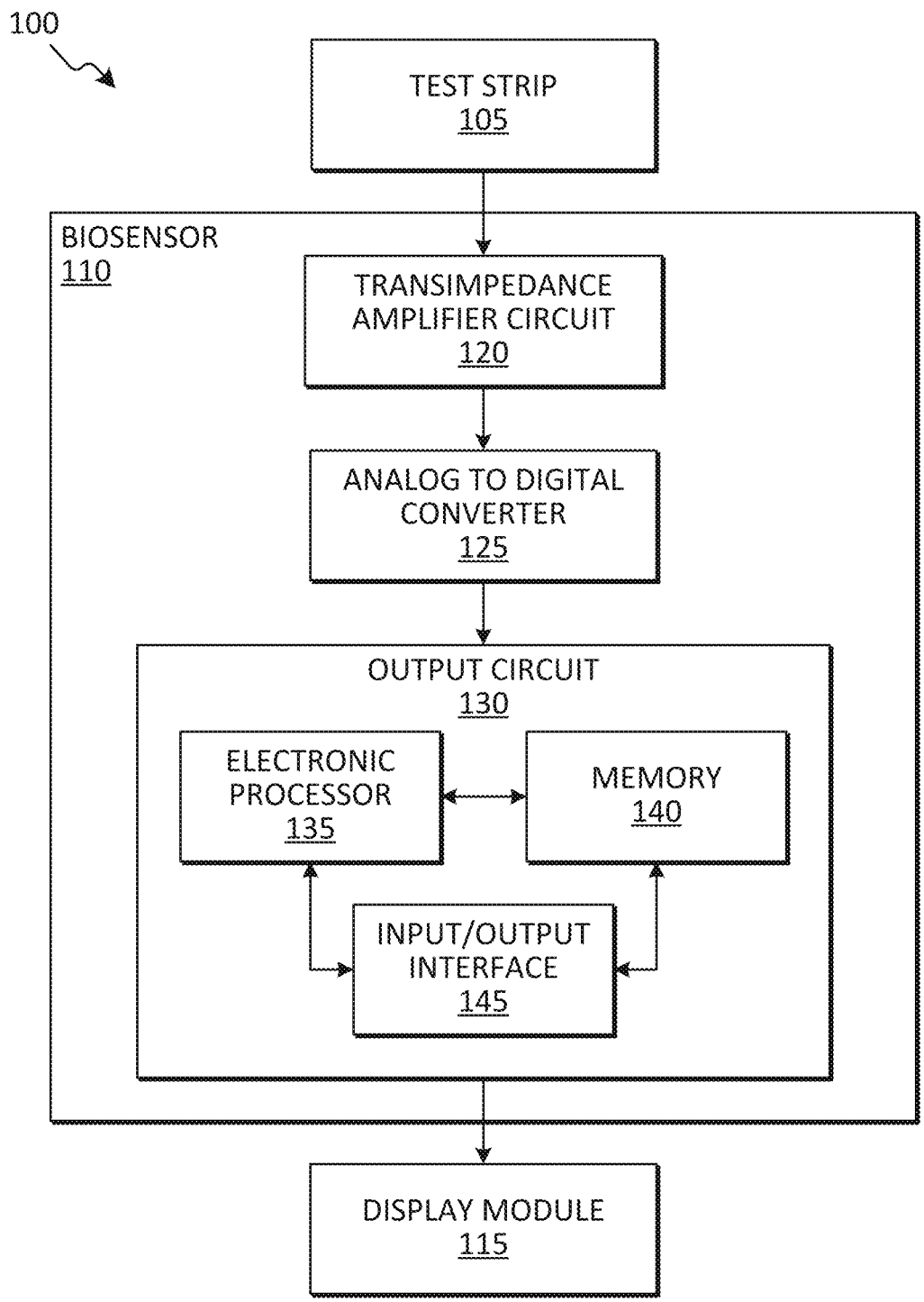
FIG. 1 is a diagram of an analyte monitoring system, in accordance with some embodiments.

FIG. 1 is a diagram of one example embodiment of an analyte monitoring system 100. In the embodiment illustrated, the analyte monitoring system 100 includes a test strip 105, a biosensor 110, and a display module 115. The test strip 105 generates electrical current due to the electrochemical reaction of an analyte on the test strip 105. For example, the test strip 105 generates electrical current due to the electrochemical reaction of glucose when blood is placed on the test strip 105.

In the embodiment illustrated, the biosensor 110 includes a transimpedance amplifier (TIA) circuit 120, an analog to digital converter 125, and an output circuit 130. In alternate embodiments, the biosensor 110 may include fewer or additional components in configurations different from the configuration illustrated in FIG. 1. As described in more detail herein, the transimpedance amplifier circuit 120 is configured to convert the electrical current generated by the electrochemical reaction of an analyte on the test strip 105 into an analog voltage signal. The analog to digital converter 125 is configured to convert the analog voltage signal to a digital voltage signal. The digital voltage signal includes digital numbers that correspond to measured levels of the analyte. For example, the digital voltage signal may include digital numbers that correspond to glucose concentrations.

In the embodiment illustrated, the output circuit 130 includes an electronic processor 135 (for example, a microprocessor, or other electronic controller), memory 140, an input/output interface 145, and a bus. In alternate embodiments, the output circuit 130 may include fewer or additional components in configurations different from the configuration illustrated in FIG. 1. The bus connects various components of the output circuit 130 including the memory 140 to the electronic processor 135. The memory 140 includes read only memory (ROM), random access memory (RAM), an electrically erasable programmable read-only memory (EEPROM), other non-transitory computer-readable media, or a combination thereof. The electronic processor 135 is configured to retrieve program instructions and data from the memory 140 and execute, among other things, instructions to perform the methods described herein. Alternatively, or in addition to, the memory 140 is included in the electronic processor 135. The input/output interface 145 includes routines for transferring information between components within the output circuit 130 and other components of the biosensor 110, as well as components external to the biosensor 110. The input/output interface 145 is configured to transmit and receive signals via wires, fiber, wirelessly, or a combination thereof. Signals may include, for example, information, data, serial data, data packets, analog signals, or a combination thereof.

The output circuit 130 is configured to transmit a signal indicating the measured level of the analyte based on the digital voltage signal. In some embodiments, the output circuit 130 determines and transmits a measured level of the analyte based on the digital voltage signal. For example, the electronic processor 135 may sample the digital voltage signal and determine a glucose concentration. The electronic processor 135 transmits a signal indicating the determined glucose concentration via the input/output interface 145. Alternatively, or in addition to, the output circuit 130 transmits the digital voltage signal. In some embodiments, the electronic processor 135 performs pre-processing (for example, filtering) prior to transmitting the digital voltage signal. For example, the electronic processor 135 applies a digital low pass filter to the digital voltage signal.

The display module 115 includes a suitable display mechanism for displaying visual output (for example, a light-emitting diode (LED) screen, a liquid crystal display (LCD) screen, and the like). In the embodiment illustrated in FIG. 1, the output circuit 130 transmits a signal to the display module 115 which causes the display module 115 to display the measured level of the analyte. For example, the display module 115 displays a glucose concentration.

The analyte monitoring system 100 illustrated in FIG. 1 is provided as one example of such a system. The transimpedance amplifier circuits described herein may be used with analyte monitoring systems with fewer, additional, or different components in different configurations than the analyte monitoring system 100 illustrated in FIG. 1. For example, in some embodiments, the analyte monitoring system 100 includes additional electronic processors.

As described above, the transimpedance amplifier circuit 120 converts and amplifies the electrical current generated by the electrochemical reaction of an analyte on the test strip 105 into an analog voltage signal. Conventional transimpedance amplifier (TIA) designs include the common gate TIA and the common source TIA.

Figure 2:
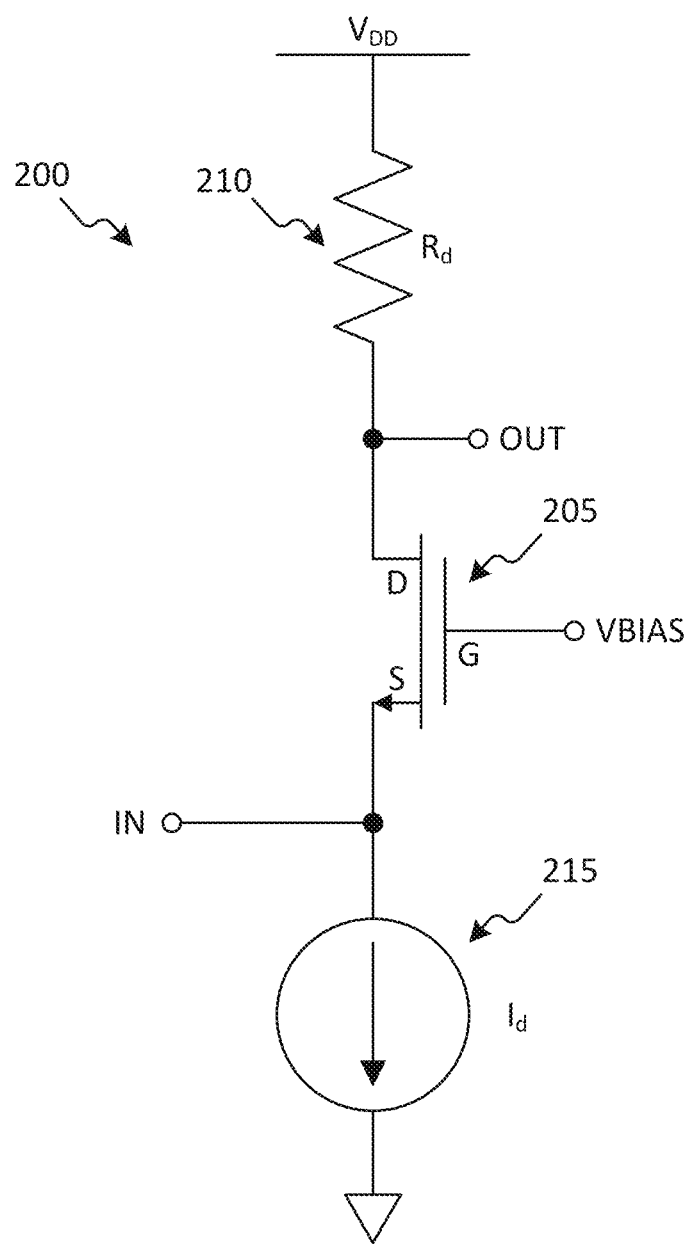
FIG. 2 is a diagram of a gate transimpedance amplifier circuit.

FIG. 2 is a diagram of one example basic implementation of a common gate TIA circuit 200. In the implementation illustrated, the common gate TIA circuit 200 includes a n-type channel metal oxide semiconductor (NMOS) transistor 205, a resistor 210, and a current source 215. An input terminal IN of the common gate TIA circuit 200 is connected to the source electrode of the NMOS transistor 205. An output terminal OUT of the common gate TIA circuit 200 is connected to the drain electrode of the NMOS transistor 205. A biasing voltage VBIAS is applied to the gate electrode of the NMOS transistor 205. The source electrode of the NMOS transistor 205 is connected to a first electrode of the current source 215. The second electrode of the current source is connected to a reference voltage terminal (for example, an electrical ground). A first electrode of the resistor 210 is connected to a power supply voltage source terminal $V_{DD}$. A second electrode of the resistor 210 is connected to the drain electrode of the NMOS transistor 205.

Neglecting second order effects in the NMOS transistor 205, the input impedance of the common gate TIA circuit 200 is $1/g_m$, where $g_m$ denotes the transconductance of the input transistor. Input referred noise of the common gate TIA circuit 200 is the primary drawback of this configuration. Thus, it is difficult with common gate TIAs to achieve reasonable transimpedance gain at low noise with low supply voltages. Since the purpose of the common gate TIA design is to have low input impedance, the input device must have a large $g_m$ which means its noise contribution is also large. The current noise density may be determined using equation (1).

$$i_n^2 = \gamma k_B T g_m \qquad (1)$$

where
$i_n^2$=noise density,
$\gamma$=a factor of transistor parameters,
$k_b$=Boltzmann's constant,
T=temperate, and
$g_m$=transconductance.

Figure 3:
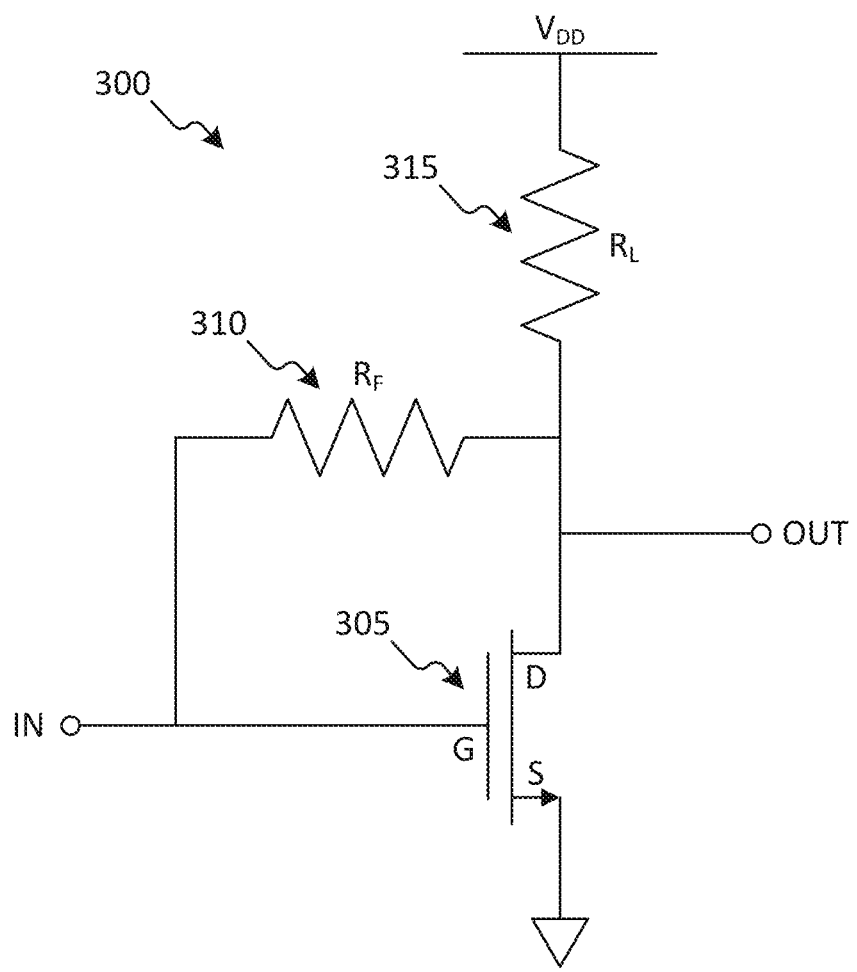
FIG. 3 is a diagram of a source transimpedance amplifier circuit.

A common source TIA is the most commonly used topology. FIG. 3 is a diagram of one example basic implementation of a common source TIA circuit 300. In the implementation illustrated, the common source TIA circuit 300 includes an NMOS transistor 305, a first resistor 310, and a second resistor 315. An input terminal IN of the common source TIA circuit 300 is connected to the gate electrode of the NMOS transistor 305. An output terminal OUT of the common source TIA circuit 300 is connected to the drain electrode of the NMOS transistor 305. A first electrode of the first resistor 310 is connected to the gate electrode of the NMOS transistor 305, while a second electrode of the first resistor 310 is connected to the drain electrode of the NMOS transistor 305. A first electrode of the second resistor 315 is connected to a power supply voltage source terminal $V_{DD}$, while a second electrode of the second resistor 315 is connected to the drain electrode of the NMOS transistor 305.

The common source TIA circuit 300 has shunt feedback resistance $R_F$ (provided by the first resistor 310), which is implemented to provide low input impedance. This type of feedback circuit minimizes input resistance and increases the bandwidth, thus yielding better drive capability. Resistive load $R_L$ (provided by the second resistor 315) is used to have wideband response and it has low gain and voltage headroom. At a low supply voltage, the load resistance degrades the transimpedance gain of the common source TIA circuit 300 due to voltage headroom. Therefore, nanoscale circuit design of common source TIA with shunt feedback and load resistance is more critical. Equations (2) and (3) represent input resistance and transimpedance gain of a common source shunt feedback TIA.

$$R_{in} = \frac{R_F + R_L}{g_m R_L + 1} \qquad (2)$$

$$R_T - \frac{g_m R_F - 1}{g_m R_L + 1} R_L \approx -R_F \qquad (3)$$

where
$R_{in}$=input resistance,
$R_T$=transimpedance gain,
$R_F$=resistance of the first resistor 310,
$R_L$=resistance of the second resistor 315, and
$g_m$=transconductance.

The trade-off between transimpedance gain and input resistance of the common source TIA with shunt feedback can be seen from equations (2) and (3). An increase in feedback resistance increases the transimpedance gain. However, increasing feedback resistance increases the input impedance which results in reduction of the input pole frequency.

Figure 4:
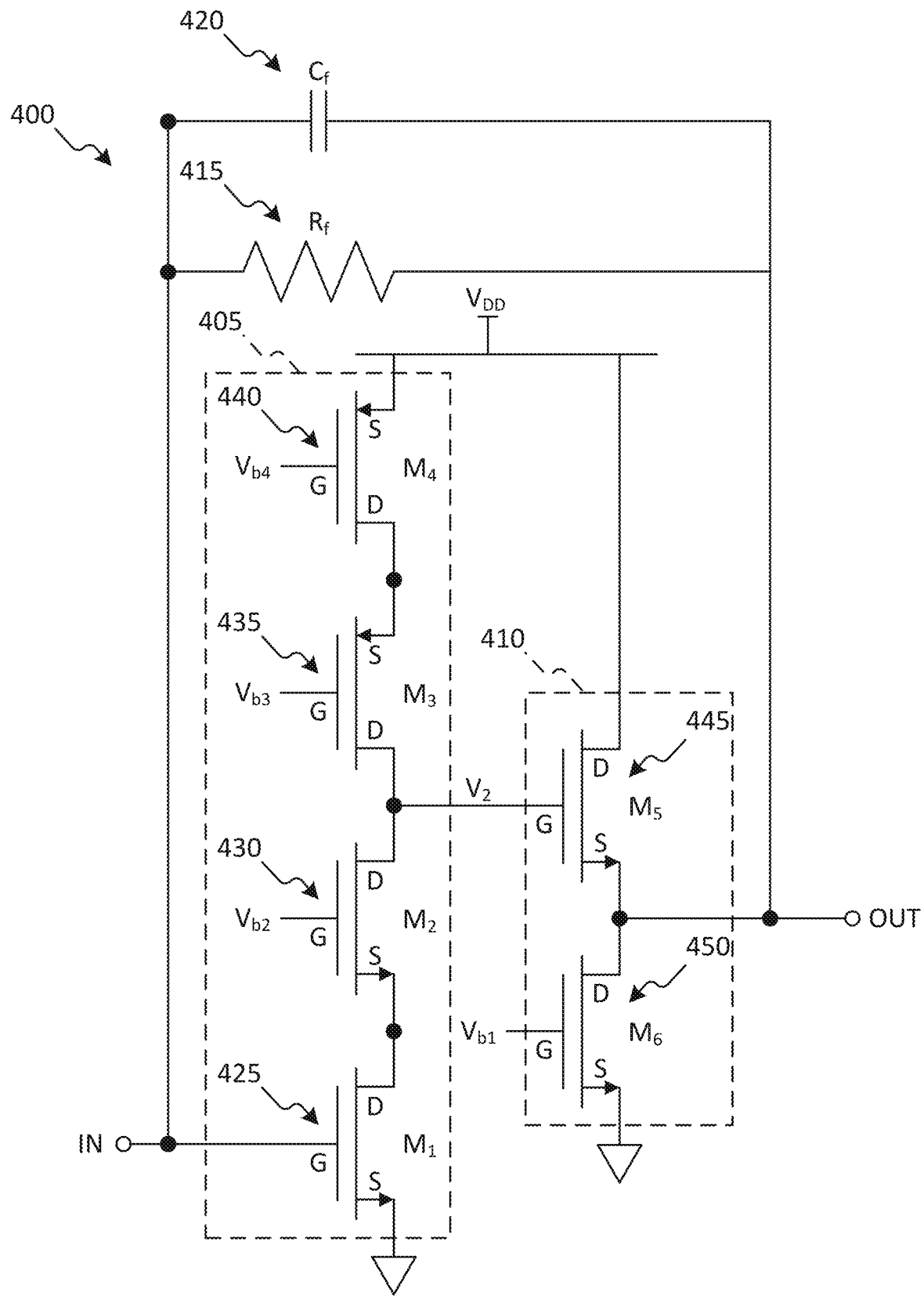
FIG. 4 is a diagram of a CMOS-based cascode common source transimpedance amplifier, in accordance with some embodiments.

FIG. 4 is a diagram of one example embodiment of a CMOS-based cascode common source TIA circuit 400 designed for 180 nanometer complementary metal oxide semiconductor (CMOS) process. Configurations, such as the one illustrated in FIG. 4, minimize noise and lower bias current requirements such that overall power dissipation is reduced. In the embodiment illustrated, the CMOS-based cascode common source TIA circuit 400 includes a first stage cascode amplifier 405, a second stage source follower 410, a resistor 415, and a capacitor 420. The first stage cascode amplifier 405 includes a first NMOS transistor 425, a second NMOS transistor 430, a first p-type channel metal oxide semiconductor (PMOS) transistor 435, and a second PMOS transistor 440. The second stage source follower 410 includes a third NMOS transistor 445 and a fourth NMOS transistor 450.

An input terminal IN of the CMOS-based cascode common source TIA circuit 400 is connected to the gate electrode of the first NMOS transistor 425. The first NMOS transistor 425 and the second NMOS transistor 430 are cascode connected. In other words, the drain electrode of the first NMOS transistor 425 is connected to the source electrode of the second NMOS transistor 430. The source electrode of the first NMOS transistor 425 is connected to a reference voltage terminal. Additionally, in the illustrated embodiment, the first PMOS transistor 435 and the second PMOS transistor 440 are cascode connected. The source electrode of the second PMOS transistor 440 is connected to a power supply voltage source terminal $V_{DD}$ such that constant current is supplied to the source electrode of the second PMOS transistor 440. The drain electrode of the second NMOS transistor 430 is connected to the drain electrode of the first PMOS transistor 435. The gate electrode of the third NMOS transistor 445 is connected to the drain electrode of the second NMOS transistor 430 and to the drain electrode of the first PMOS transistor 435. The drain electrode of the third NMOS transistor 445 is connected to the power supply voltage source terminal $V_{DD}$ such that constant current is supplied to the drain electrode of the third NMOS transistor 445. With this configuration, the third NMOS transistor 445 acts as a source follower amplifier to lower the output impedance of the first stage cascode amplifier 405. The source electrode of the third NMOS transistor 445 is connected to the drain electrode of the fourth NMOS transistor 450 to mirror current. The source electrode of the fourth NMOS transistor 450 is connected to the reference voltage terminal. An output terminal OUT of the CMOS-based cascode common source TIA circuit 400 is connected to the source electrode of the third NMOS transistor 445 and to the drain electrode of the fourth NMOS transistor 450.

The first NMOS transistor 425 and the second NMOS transistor 430 are cascode connected transistors which give the main gain of the core amplifier. The second PMOS transistor 440 is a constant current source transistor. The first PMOS transistor 435 is cascode connected to the second PMOS transistor 440 to boost the output impedance of the second PMOS transistor 440. To lower the output impedance of the cascode stage, a source follower amplifier is connected to the output of the first stage. The third NMOS transistor 445 is the source follower amplifier which is connected to the fourth NMOS transistor 450. The fourth NMOS transistor 450 is a current mirror transistor. The cascode configuration consisting of the first NMOS transistor 425 and the second NMOS transistor 430 has a high output resistance and the cascode load is replaced by a cascode current source load as shown in FIG. 4.

The resistor 415 is a feedback resistor, which is implemented to minimize the input resistance and increase the bandwidth of the CMOS-based cascode common source TIA circuit 400. A first electrode of the resistor 415 is connected to the input terminal IN of the CMOS-based cascode common source TIA circuit 400. A second electrode of the resistor 415 is connected to the output terminal OUT of the CMOS-based cascode common source TIA circuit 400. In some embodiments, the resistor 415 includes one or more polysilicon resistors.

The capacitor 420 is a compensation capacitor, which is implemented to minimize the input resistance and increase the bandwidth of the CMOS-based cascode common source TIA circuit 400. A first electrode of the capacitor 420 is connected to the input terminal IN of the CMOS-based cascode common source TIA circuit 400. A second electrode of the capacitor 420 is connected to the output terminal OUT of the CMOS-based cascode common source TIA circuit 400. In some embodiments, the capacitor 420 includes one or more metal oxide metal capacitors (MIMCAPs).

Figure 5:
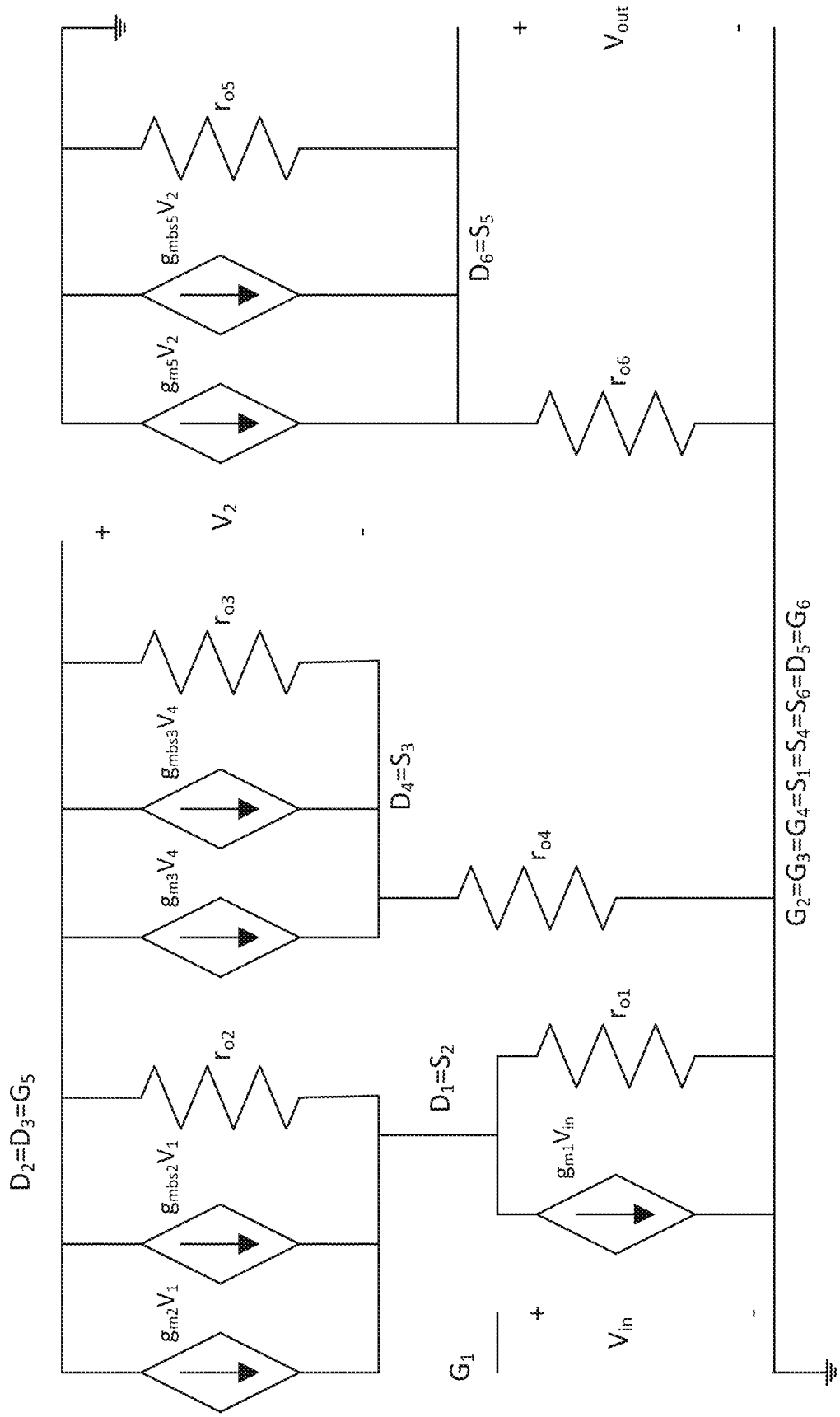
FIG. 5 is a small signal analysis model of the CMOS-based cascode common source transimpedance amplifier circuit included in FIG. 4, in accordance with some embodiments.

FIG. 5 is a diagram of an example small signal equivalence circuit model of the CMOS-based first stage cascode amplifier 405 and second stage source follower 410. The combination of both the first stage cascode amplifier 405 and the second stage source follower 410 is a cascode common source amplifier. The small-signal output resistance can be determined, for example, using equation (4).

$$R_{out2}=(g_{m2}r_{o2}r_{o1})\|(g_{m3}r_{o3}r_{o4}) \quad (4)$$

where
$R_{out2}$=small-signal output resistance,
$g_{m2}$=transconductance of the second NMOS transistor 430,
$g_{m3}$=transconductance of the first PMOS transistor 435,
$r_{o1}$=output resistance of the first NMOS transistor 425,
$r_{o2}$=output resistance of the second NMOS transistor 430,
$r_{o3}$=output resistance of the first PMOS transistor 435, and
$r_{o4}$=output resistance of the second PMOS transistor 440.

The gain from node $V_{in}$ to $V_2$ can be used to determine the open loop gain of the cascode amplifier. For example, the open loop gain of the cascode amplifier may be determined using equations (5) and (6).

$$A_{V2}=g_{m1}[(g_{m2}r_{o2}r_{o1})\|(g_{m3}r_{o3}r_{o4})] \quad (5)$$

$$A_{V2} = \frac{V_2}{V_{in}} = \left(-g_{m1}\frac{g_{m2}g_{m3}r_{o1}r_{o2}r_{o3}r_{o4}}{g_{m2}r_{o2}r_{o1}+g_{m3}r_{o3}r_{o4}}\right) \quad (6)$$

where
$A_{V2}$=gain from node $V_{in}$ to $V_2$,
$g_{m1}$=transconductance of the first NMOS transistor 425,
$g_{m2}$=transconductance of the second NMOS transistor 430,
$g_{m3}$=transconductance of the first PMOS transistor 435,
$r_{o1}$=output resistance of the first NMOS transistor 425,
$r_{o2}$=output resistance of the second NMOS transistor 430,
$r_{o3}$=output resistance of the first PMOS transistor 435,
$r_{o4}$=output resistance of the second PMOS transistor 440,
$V_2$=voltage at the output of the first stage cascode amplifier 405, and
$V_{in}$=voltage at the input terminal IN.

The source follower gain can be used determine the gain from $V_{in}$ to $V_{out}$. For example, the source follower gain can be determined using equation (7).

$$A_{V3} = \frac{V_{out}}{V_2} = \left(\frac{g_{m6}}{g_{m6}+g_{mb6}}\right) \le 1 \quad (7)$$

where
$A_{V3}$=gain from node $V_{out}$ to $V_2$,
$V_{out}$=voltage at the output terminal OUT,
$V_2$=voltage at the output of the first stage cascode amplifier 405,
$g_{m6}$=transconductance of the fourth NMOS transistor 450, and
$g_{mb6}$=backgate transconductance of the fourth NMOS transistor 450.

By substituting equations (6) and (7), the open loop gain of the cascode common source amplifier can be determined using equation (8).

$$A_V = A_{V2} \cdot A_{V3} = \frac{V_{out}}{V_{in}} = \left(-g_{m1}\frac{g_{m2}g_{m3}r_{o1}r_{o2}r_{o3}r_{o4}}{g_{m2}r_{o2}r_{o1}+g_{m3}r_{o3}r_{o4}}\right) \quad (8)$$

where
$A_V$=open loop gain of the CMOS-based cascode common source TIA circuit 400,
$A_{V2}$=gain from node $V_{in}$ to $V_2$,
$A_{V3}$=gain from node $V_{out}$ to $V_2$,
$V_{out}$=voltage at the output terminal OUT,
$V_{in}$=voltage at the input terminal IN, $g_{m1}$=transconductance of the first NMOS transistor 425, $g_{m2}$=transconductance of the second NMOS transistor 430, $g_{m3}$=transconductance of the first PMOS transistor 435, $r_{o1}$=output resistance of the first NMOS transistor 425, $r_{o2}$=output resistance of the second NMOS transistor 430, $r_{o3}$=output resistance of the first PMOS transistor 435, and $r_{o4}$=output resistance of the second PMOS transistor 440.

The voltage noise of the amplifier is one example factor to achieve a lower noise. For simplification, the noise contribution of the source follower may be neglected. The input referred voltage noise of the cascode amplifier can be determined, for example, using equations (9) and (10).

$$V_{n,in}^2 = \frac{I_{n1}^2}{g_{m1}^2} + \frac{I_{n2}^2 r_{o2}^2}{g_{m2}^2 g_{m1}^2 r_{o1}^2 r_{o2}^2} + \frac{I_{n3}^2 r_{o3}^2}{g_{m3}^2 g_{m1}^2 r_{o4}^2 r_{o3}^2} + \frac{I_{n4}^2}{g_{m1}^2} \quad (9)$$

$$V_{n,in}^2 = \frac{4kT\gamma}{g_{m1}} + \frac{4kT\gamma}{g_{m2}^2 g_{m1}^2 r_{o1}^2} + \frac{4kT\gamma}{g_{m3}^2 g_{m1}^2 r_{o4}^2} + \frac{4kT\gamma g_{m4}}{g_{m1}^2} \quad (10)$$

where $V_{n,in}^2$=open loop gain of the CMOS-based cascode common source TIA circuit 400, $I_{n1}^2$=current noise of the first NMOS transistor 425, $I_{n2}^2$=current noise of the second NMOS transistor 430, $I_{n3}^2$=current noise of the first PMOS transistor 435, $I_{n4}^2$=current noise of the second PMOS transistor 440, $g_{m1}^2$=transconductance of the first NMOS transistor 425, $g_{m2}^2$=transconductance of the second NMOS transistor 430, $g_{m3}^2$=transconductance of the first PMOS transistor 435, $r_{o1}^2$=output resistance of the first NMOS transistor 425, $r_{o2}^2$=output resistance of the second NMOS transistor 430, $r_{o3}^2$=output resistance of the first PMOS transistor 435, $r_{o4}^2$=output resistance of the second PMOS transistor 440, k=Boltzmann constant, T=temperature, and γ=a factor of transistor parameters.

Figure 6:
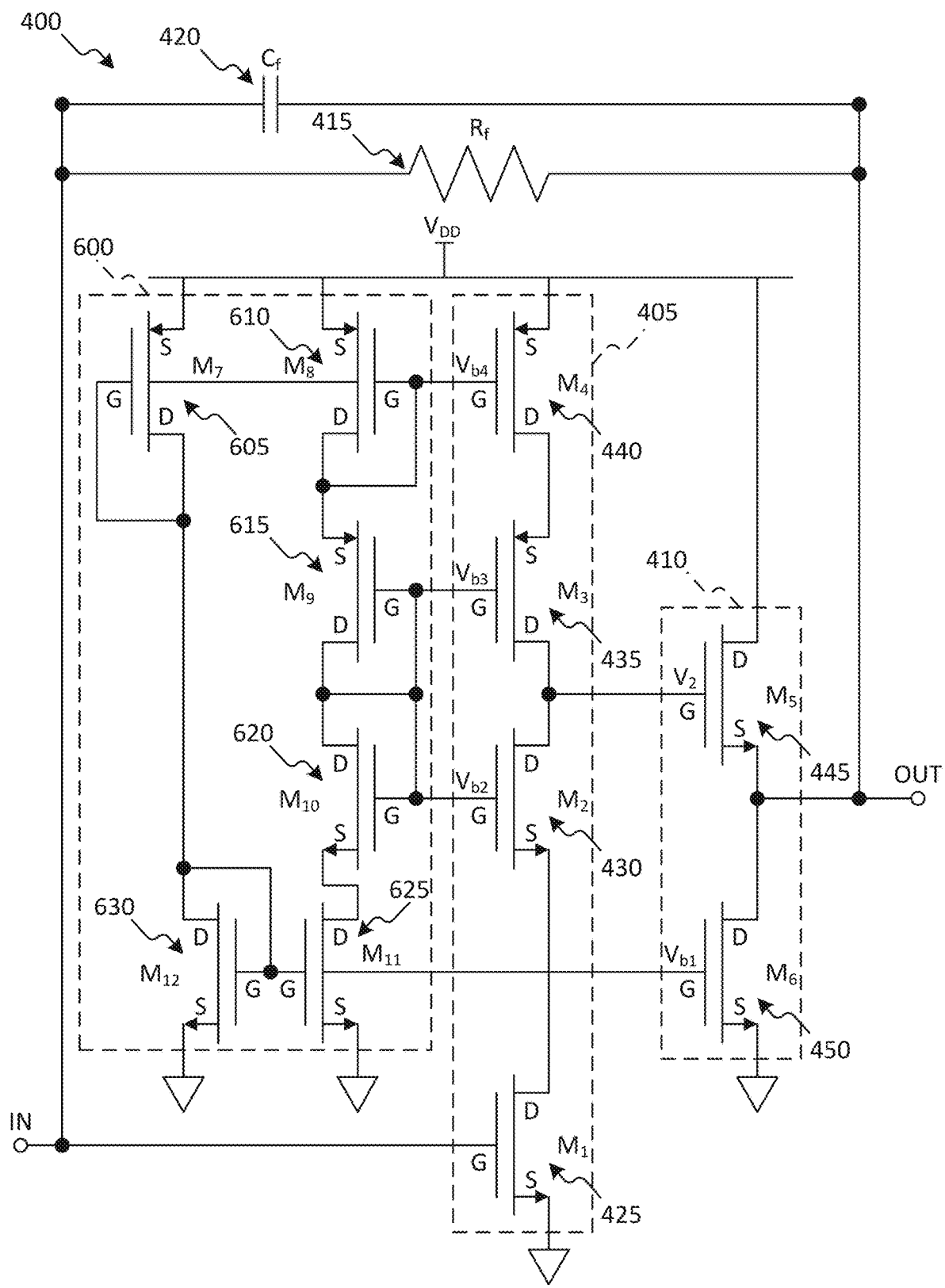
FIG. 6 is a diagram of the CMOS-based cascode common source transimpedance amplifier circuit included in FIG. 4 with a biasing circuit, in accordance with some embodiments.

FIG. 6 is diagram of one example embodiment of a biasing circuit 600 included in some embodiments of the CMOS-based cascode common source TIA circuit 400. The biasing circuit 600 includes a third PMOS transistor 605, a fourth PMOS transistor 610, a fifth PMOS transistor 615, a fifth NMOS transistor 620, a sixth NMOS transistor 625, and a seventh NMOS transistor 630. The transistors included in the biasing circuit 600 are made to operate in the saturation region to achieve maximum gain. The biasing circuit 600 is designed using current mirror technique. The sizes of the current mirrors and the cascode amplifier are the same to minimize the effect of channel length modulation.

The first bias voltage $V_{b1}$ for the fourth NMOS transistor 450 is generated by the sixth NMOS transistor 625 and the seventh NMOS transistor 630. There is no DC current flow over the resistor 415. Therefore, the voltage between the drain electrode and the source electrode of the fourth NMOS transistor 450, the voltage at the output terminal OUT, the voltage at the input terminal IN, and the voltage between gate electrode and the source electrode of the first NMOS transistor 425 are all equal. In view of this, the bias condition for the fourth NMOS transistor 450 can be determined using equation (11).

$$V_{gs1} > V_{b1} - V_{tn6} \quad (11)$$

where $V_{gs1}$=gate to source voltage of the first NMOS transistor 425, $V_{b1}$=first bias voltage $V_{b1}$ for the fourth NMOS transistor 450, and $V_{tn6}$=threshold voltage of the fourth NMOS transistor 450.

The second bias voltage $V_{b2}$ for the second NMOS transistor 430 is generated by the fifth NMOS transistor 620. The saturation condition for the second NMOS transistor 430 can be determined using equations (12) and (13).

$$V_{ds2} > V_{gs2} - V_{tn2} \quad (12)$$

$$V_{gs1} + V_{gs5} + V_{tn2} > V_{b2} > V_{gs2} + V_{gs1} - V_{tn1} \quad (13)$$

where $V_{ds2}$=drain to source voltage of the second NMOS transistor 430, $V_{gs2}$=gate to source voltage of the second NMOS transistor 430, $V_{tn2}$=threshold voltage of the second NMOS transistor 430, $V_{gs1}$=gate to source voltage of the first NMOS transistor 425, $V_{gs5}$=gate to source voltage of the third NMOS transistor 445, and $V_{b2}$=bias voltage for the second NMOS transistor 430.

In some embodiments, the size of the fifth NMOS transistor 620 is equal to the second NMOS transistor 430 such that the second bias voltage $V_{b2}$ is equal to the gate to source voltage of the fifth NMOS transistor 620. In such embodiments, the second bias voltage $V_{b2}$ is greater than the gate to source voltage of the second NMOS transistor 430 plus the gate to the source voltage of the first NMOS transistor 425 minus the threshold voltage of the first NMOS transistor 425, and the first NMOS transistor 425 and the second NMOS transistor 430 will be in saturation if the condition defined by equation (14) is met.

$$V_{gs5} > V_{gs2} - V_{tn2} \quad (14)$$

where $V_{gs5}$=gate to source voltage of the third NMOS transistor 445, $V_{gs2}$=gate to source voltage of the second NMOS transistor 430, and $V_{tn2}$=threshold voltage of the second NMOS transistor 430.

The third bias voltage $V_{b3}$ and the fourth bias voltage $V_{b4}$ are generated by the fifth PMOS transistor 615 and the fourth PMOS transistor 610. The gate electrode of the first PMOS transistor 435 is connected to the gate electrode of the fifth PMOS transistor 615. The gate of the second PMOS transistor 440 is connected to the gate electrode of the fourth PMOS transistor 610. The saturation conditions for the fifth PMOS transistor 615 and the fourth PMOS transistor 610 can be determined using equations (15) and (16).

$$V_{sd4} > V_{sg4} - V_{tp4}$$

$$V_{dd} - V_3 > V_{dd} - V_{b4} - V_{tp4}$$

$$V_3 < V_{b4} + V_{tp4} \quad (15)$$

$$V_{b3} = V_3 + V_{sg3}$$

$$V_{b4} - V_{b3} > V_{sg3} - V_{tp4} \quad (16)$$

where
- $V_{sd4}$=source to drain voltage of the second PMOS transistor 440,
- $V_{sg4}$=source to gate voltage of the second PMOS transistor 440,
- $V_{tp4}$=threshold voltage of the second PMOS transistor 440,
- $V_{dd}$=power supply voltage,
- $V_3$=voltage between the third PMOS transistor 435 and the fourth PMOS transistor 440,
- $V_{b4}$=bias voltage for the second PMOS transistor 440,
- $V_{b3}$=bias voltage for the first PMOS transistor 435, and
- $V_{sg3}$=source to gate voltage of the first PMOS transistor 435.

Figure 7:
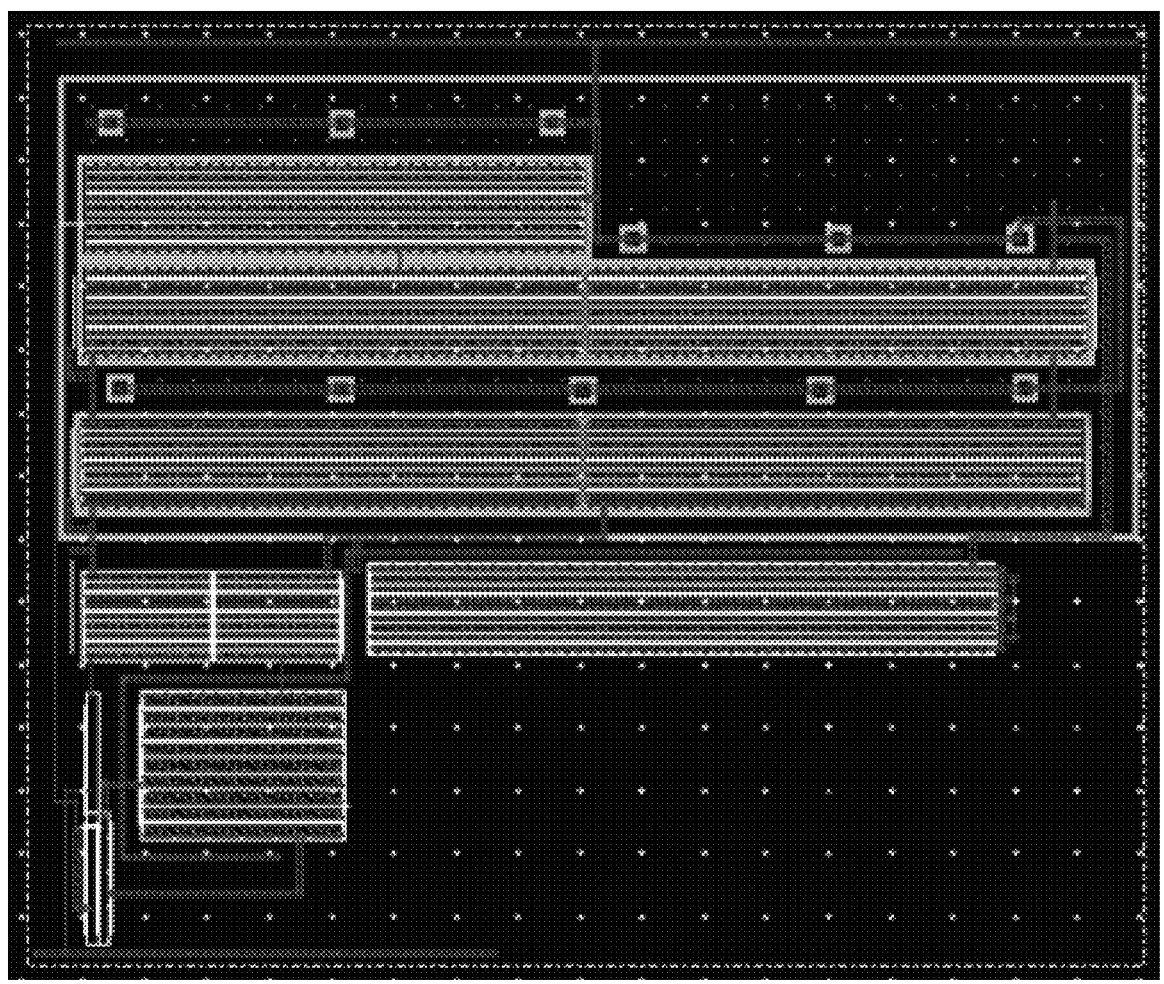
FIG. 7 is a layout design of the CMOS-based cascode common source transimpedance amplifier circuit and the biasing circuit included in FIG. 6, in accordance with some embodiments.

FIG. 7 is an example layout design of one embodiment of the CMOS-based cascode common source TIA circuit 400 using a generic process design kit 180 nanometer CMOS model.

In some embodiments, the MOSFETs described herein are replaced by carbon nanotube field effect transistor (CNTFETs). Carbon nanotubes possess unique mechanical, electrical, and thermal properties. Carbon nanotubes have greater thermal conductivity and excellent current density. The carbon nanotube is a sheet of graphite which is rolled up along a direction in which the thin layer of carbon is arranged. The chirality of a carbon nanotube can be determined using equation (17).

$$C_h = a\sqrt{n_1^2 + n_2^2 + n_1 n_2} \tag{17}$$

where
- $C_h$=chirality of the carbon nanotube,
- a=lattice constant of carbon,
- $n_1$=positive integers, and
- $n_2$=positive integers.

The diameter of a carbon nanotube can be determined using equation (18).

$$D_{CNT} = C_h/\pi \tag{18}$$

where
- $D_{CNT}$=diameter of the carbon nanotube (for example, 1.5 nanometers), and
- $C_h$=chirality of the carbon nanotube.

Figure 8:
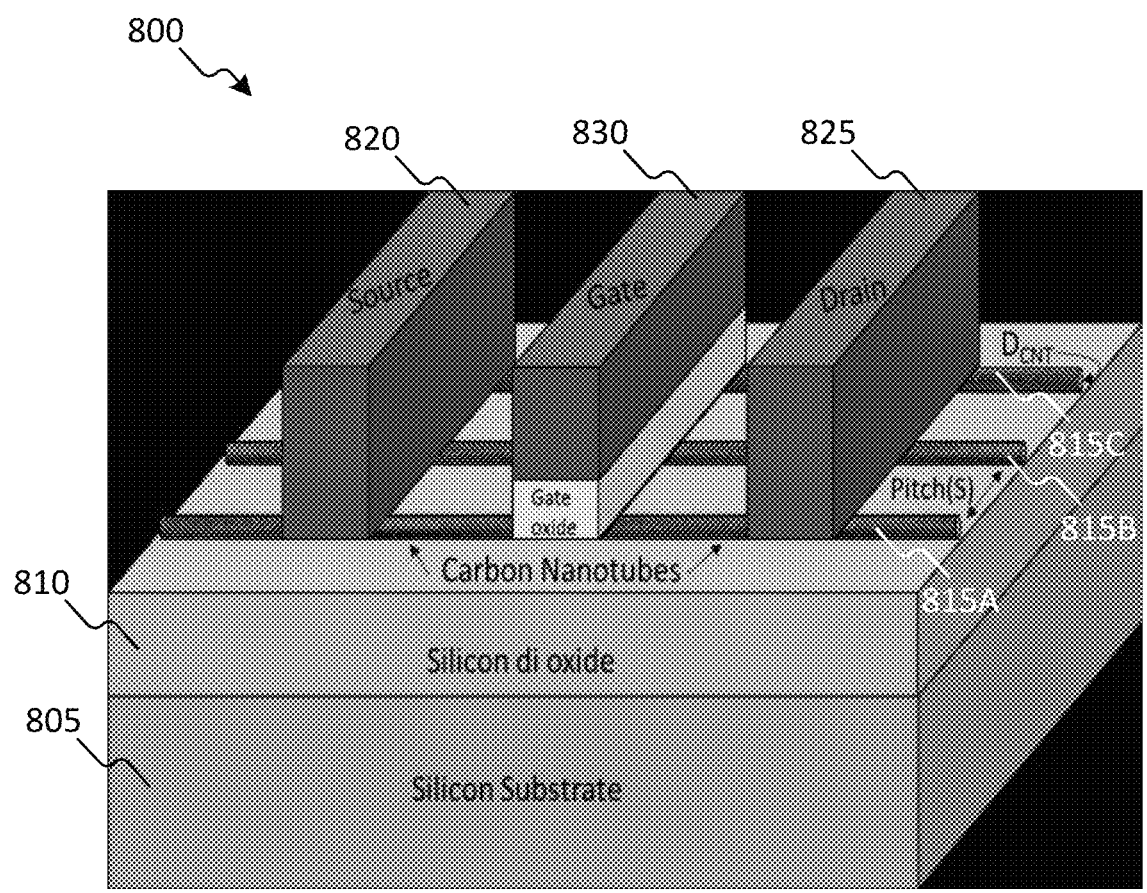
FIG. 8 is a diagram of a carbon nanotube (CNT) field effect transistor, in accordance with some embodiments.

CNTFETs possess high device current carrying ability and have a great potential to replace MOSFETs. In a CNTFET, the channel between the source and drain regions is created by using a parallel combination of carbon nanotubes. FIG. 8 is an example embodiment of a CNTFET 800. In the embodiment illustrated, the CNTFET 800 includes a substrate layer 805 (for example, silicon), an oxide layer 810 (for example, silicon dioxide), a plurality of carbon nanotubes 815A-C, a source region 820, a drain region 825, and a gate region 830. The plurality of carbon nanotubes 815A-C are arranged parallel to each other in a channel as illustrated in FIG. 8. The source region 820 and the drain region 825 are heavily doped. The plurality of carbon nanotubes 815A-C are undoped. The number of carbon nanotubes in the channel has a significant impact on the overall performance of a CNTFET. Increasing the number of carbon nanotubes in the channel of a CNTFET is equivalent to increasing the channel width of the CNTFET, which significantly increases the drain current. The working principle of a CNTFET is similar to that of a MOSFET. For example, CNTFETs are voltage controlled devices, with gate voltages controlling the drain current, and the gate is capacitively coupled with the channel.

A CNTFET has many advantages, such as better transport properties with one dimensional (1D) ballistic transport of charge carriers. The ballistic transport results in high mobility and large driving current (about three to four times higher than that of a MOSFET). Additionally, a CNTFET has large transconductance, low intrinsic capacitance, near ideal subthreshold slope, and strong covalent bonding. Due the strong covalent bonding of atoms, a CNTFET has high current density and high mobility due to lack of surface states in the tube. The performance of CNTFET can be improved by optimizing various parameters of the carbon nanotubes, such as the number of carbon nanotubes, the inter carbon nanotube pitch, and the diameter of a carbon nanotube. The channel width of the carbon nanotube can be determined using equation (19).

$$W = (N-1)S + D_{CNT} \tag{19}$$

where
- W=channel width (for example, 64 nanometers),
- N=number of carbon nanotubes on the channel (for example, three),
- S=inter carbon nanotube pitch (for example, 20 nanometers), and
- $D_{CNT}$=diameter of the carbon nanotube (for example, 1.5 nanometers).

The energy bandgap of a carbon nanotube can be determined using equation (20).

$$E_g = \frac{2a_{cc}t}{D_{CNT}} = \frac{0.84\text{eV}}{D_{CNT}} = 2\text{eV}_{th} \tag{20}$$

where
- $E_g$=energy bandgap,
- $a_{cc}$=distance between the carbon to carbon bond (for example, 0.1412 nanometers),
- t=energy between the carbon to carbon bond (for example, 3 electron volts),
- $D_{CNT}$=diameter of the carbon nanotube (for example, 1.5 nanometers),
- e=unit electron charge, and
- $V_{th}$=voltage threshold.

As shown in equation (20), the threshold voltage of a CNTFET is inversely dependent on the diameter of the carbon nanotube. Hence, the threshold voltage in a CNTFET can be adjusted by changing the carbon nanotube diameter. This adjustability makes CNTFETs well suited for ultra-low-power circuits. In some embodiments, the length of the carbon nanotube is 32 nanometers. In some embodiments, the gate dielectric thickness is 3 nanometers. In some embodiments, the gate dielectric constant is 16. In some embodiments, the source dielectric thickness is 10 micrometers. In some embodiments, the source dielectric constant is 3.9. In some embodiments, the coupling capacitance is 7 picofarads.

Figure 9:
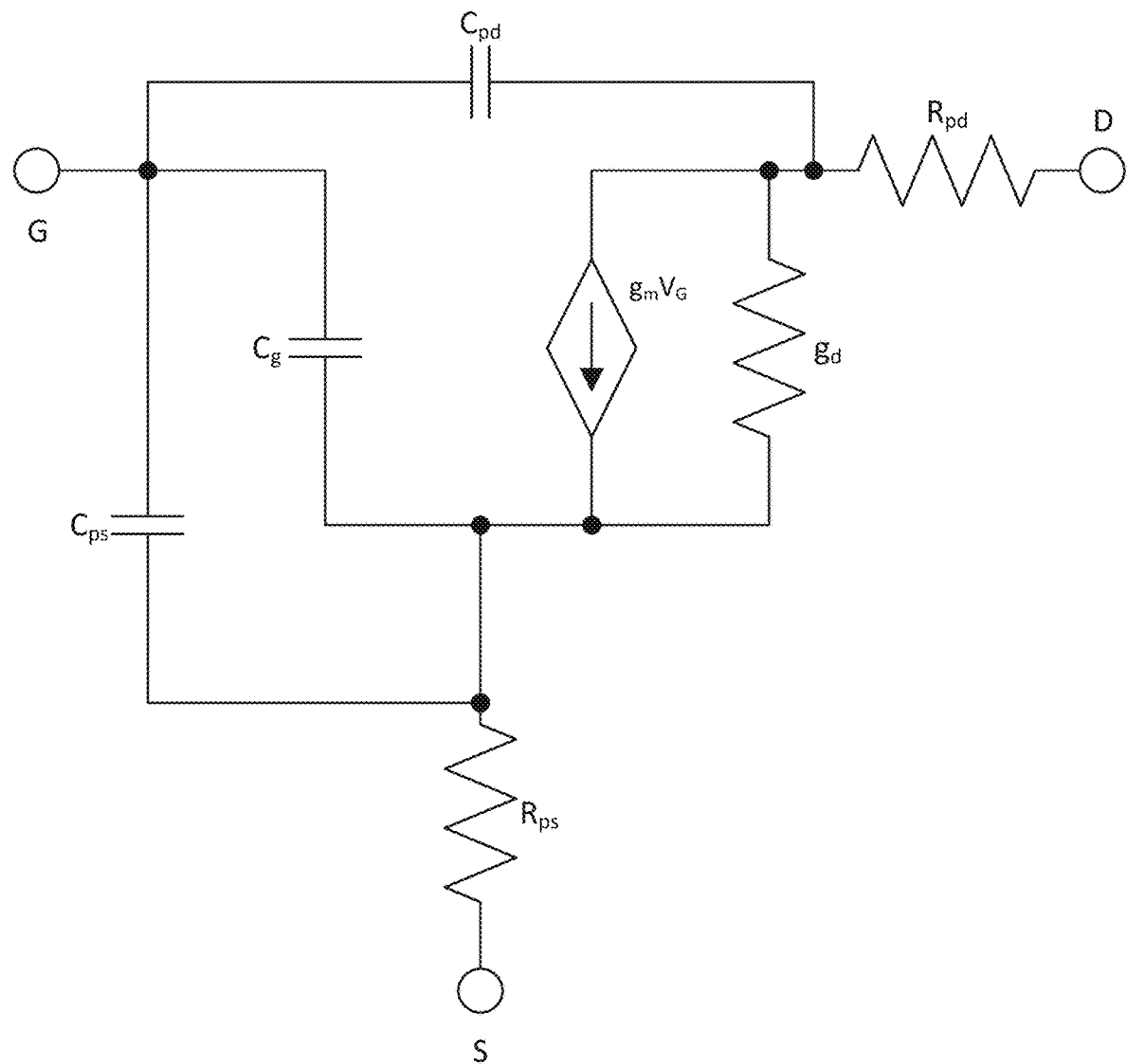
FIG. 9 is a small signal analysis model of the carbon nanotube field effect transistor included in FIG. 8, in accordance with some embodiments.

FIG. 9 is an example embodiment of a small-signal equivalent model of a CNTFET. $g_d$ is the channel conductance (i.e., the source to drain conductance), $C_{ps}$ is the parasitic capacitance between gate and source, $C_{pd}$ is the parasitic capacitance between gate and drain electrodes are obtained by electrostatic calculations, $R_{ps}$ is the parasitic source resistance, and $R_{pd}$ is the parasitic drain resistance. The transconductance $g_m$, the intrinsic gate capacitance $C_g$, and the source to drain conductance $g_d$ of a CNTFET can be determined using equations (21), (22), and (23).

$$g_m = \frac{\partial I_d}{\partial V_g}\bigg|_{V_d} \tag{21}$$

$$C_g = \frac{\partial Q_{ch}}{\partial V_g}\bigg|_{V_d} \tag{22}$$

$$g_d = \frac{\partial I_d}{\partial V_d}\bigg|_{V_g} \tag{23}$$

where
- $g_m$=transconductance,
- $I_d$=source to drain current,
- $V_g$=gate voltage,
- $V_d$=drain voltage,
- $C_g$=intrinsic gate capacitance,
- $Q_{th}$=total charge in the carbon nanotube channel, and
- $g_d$=source to drain conductance.

The small signal equivalent model describes the I-V characteristics of the CNTFET by keeping the linear terms of a Taylor expansion for source to drain current, which is given in equation (24) indicates the transconductance is in parallel with the channel conductance.

$$dI_D \approx \frac{\partial I_D}{\partial V_D}dV_D + \frac{\partial I_D}{\partial V_D}dV_G = g_d dV_D + g_m dV_G \tag{24}$$

where
- $I_D$=source to drain current,
- $V_D$=drain voltage,
- $V_G$=gate voltage, and
- $g_m$=transconductance.

Additional elements are added to the equivalent circuit to take parasitic capacitances and resistances into account. The parasitic capacitance $C_{ps}$ between the gate and source electrodes and the parasitic capacitance $C_{pd}$ between gate and drain electrodes can be determined by a separate electrostatic calculation, because the size of the contacts can be much larger than the size of the carbon nanotube channel. Because the parasitic capacitances between the metal gate electrode, the metal source electrode, and the drain electrode are nearly bias-independent, they can be treated as constant electrostatic capacitances.

Figure 10:
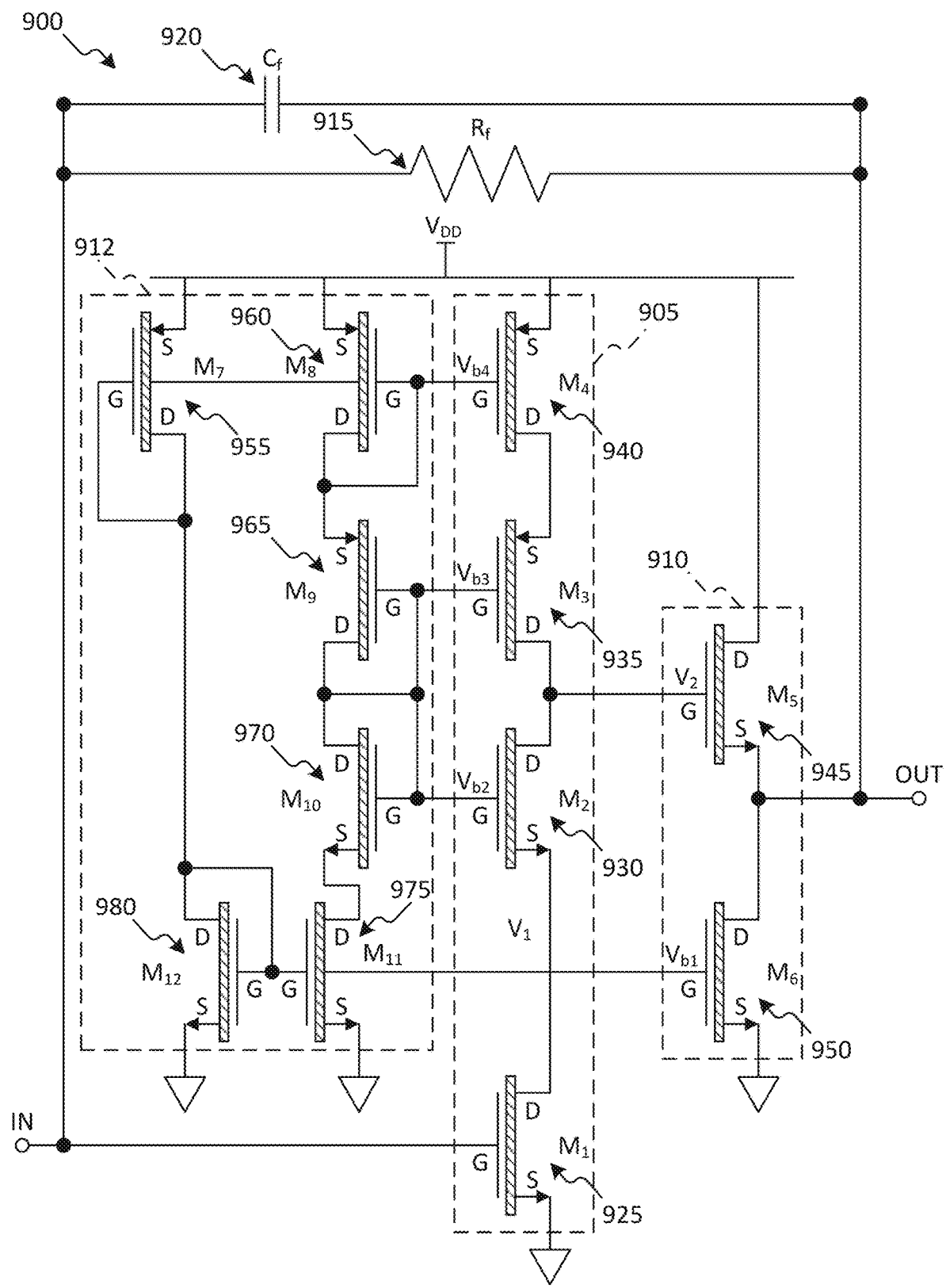
FIG. 10 is a diagram of a CNT-based cascode common source transimpedance amplifier circuit and a biasing circuit, in accordance with some embodiments.

FIG. 10 is a diagram of one example embodiment of a CNT-based cascode common source TIA circuit 900 designed for 32 nanometer carbon nanotubes process at 1.8 volts. In the embodiment illustrated, the CNT-based cascode common source TIA circuit 900 includes a first stage cascode amplifier 905, a second stage source follower 910, a biasing circuit 912, a resistor 915, and a capacitor 920. The first stage cascode amplifier 905 includes a first n-type channel carbon nanotube field effect transistor (NCNTFET) 925, a second NCNTFET 930, a first p-type channel carbon nanotube field effect transistor (PCNTFET) 935, and a second PCNTFET 940.

An input terminal IN of the CNT-based cascode common source TIA circuit 900 is connected to the gate electrode of the first NCNTFET 925. The first NCNTFET 925 and the second NCNTFET 930 are cascode connected. In other words, the drain electrode of the first NCNTFET 925 is connected to the source electrode of the second NCNTFET 930. The source electrode of the first NCNTFET 925 is connected to a reference voltage terminal. The first PCNTFET 935 and the second PCNTFET 940 are cascode connected. The source electrode of the second PCNTFET 940 is connected to a power supply voltage source terminal $V_{DD}$ such that constant current is supplied to the source electrode of the second PCNTFET 940. The drain electrode of the second NCNTFET 930 is connected to the drain electrode of the first PCNTFET 935.

The second stage source follower 910 includes a third NCNTFET 945 and a fourth NCNTFET 950. The gate electrode of the third NCNTFET 945 is connected to the drain electrode of the second NCNTFET 930 and to the drain electrode of the first PCNTFET 935. The drain electrode of the third NCNTFET 945 is connected to the power supply voltage source terminal $V_{DD}$ such that constant current is supplied to the drain electrode of the third NCNTFET 945. With this configuration, the third NCNTFET 945 acts as a source follower amplifier to lower the output impedance of the first stage cascode amplifier 905. The source electrode of the third NCNTFET 945 is connected to the drain electrode of the fourth NCNTFET 950 to mirror current. The source electrode of the fourth NCNTFET 950 is connected to the reference voltage terminal. An output terminal OUT of the CNT-based cascode common source TIA circuit 900 is connected to the source electrode of the third NCNTFET 945 and to the drain electrode of the fourth NCNTFET 950.

The first NCNTFET 925 and the second NCNTFET 930 are cascode connected transistors which give the main gain of the core amplifier. The second PCNTFET 940 is a constant current source transistor. The first PCNTFET 935 is cascode connected to the second PCNTFET 940 to boost the output impedance of the first stage cascode amplifier 905. The second stage source follower 910, which is composed of the third NCNTFET 945 and the fourth NCNTFET 950, is connected to the output of the first stage cascode amplifier 905 to improve overall gain performance.

The biasing circuit 912 includes a third PCNTFET 955, a fourth PCNTFET 960, a fifth PCNTFET 965, a fifth NCNTFET 970, a sixth NCNTFET 975, and a seventh NCNTFET 980. The first bias voltage $V_{b1}$ for the fourth NCNTFET 950 is generated by the sixth NCNTFET 975 and the seventh NCNTFET transistor 980. The second bias voltage $V_{b2}$ for the second NCNTFET 930 is generated by the fifth NCNTFET 970. The third bias voltage $V_{b3}$ for the first PCNTFET 935 is generated by the fifth PCNTFET 965. The fourth bias voltage $V_{b4}$ for the second PCNTFET 940 is generated by the fourth PCNTFET 960.

The resistor 915 is a feedback resistor. A first electrode of the resistor 915 is connected to the input terminal IN of the CNT-based cascode common source TIA circuit 900. A second electrode of the resistor 915 is connected to the output terminal OUT of the CNT-based cascode common source TIA circuit 900. In some embodiments, the resistor 915 includes one or more polysilicon resistors.

The capacitor 920 is a compensation capacitor. A first electrode of the capacitor 920 is connected to the input terminal IN of the CNT-based cascode common source TIA circuit 900. A second electrode of the capacitor 920 is connected to the output terminal OUT of the CNT-based cascode common source TIA circuit 900. In some embodiments, the capacitor 920 includes one or more metal oxide metal capacitors (MIMCAPs).

In general, the gain, speed, and power dissipation of a CMOS based TIA degrades when the technology is scaled down. The CNT-based cascode common source TIA circuit 900 is a combination of different classes of amplifiers, where cascoding significantly improves the transimpedance amplifier gain and bandwidth performance. Thus, the CNT-based cascode common source TIA circuit 900 has higher input impedance, higher input-output isolation, higher gain, is more stable, and dissipates ultra-low-power compared to CMOS-based TIAs. Additionally, high integration circuits with low power can be designed with the CNT-based cascode common source TIA circuit 900. The performance of the CNT-based cascode common source TIA circuit 900 increases initially with increases in number of carbon nanotubes, and later on saturates. The variation in the number of carbon nanotubes affects DC gain, average power, frequency, and output resistance. The initial increase in DC gain can be attributed to the increase in drive capability of both the NCNTFETs and the PCNTFETs. As show in equation (25), the driving capability of a CNTFET increases significantly as the number of carbon nanotubes increases.

$$I_{CNTFET} \approx N g_{CNT}(V_{dd}-V_{th})/(1+g_{CNT}L_s\rho_s) \quad (25)$$

where
- $I_{CNTFET}$=CNTFET ON current,
- N=number of carbon nanotubes,
- $g_{CNT}$=transconductance per carbon nanotube,
- $V_{dd}$=power supply voltage,
- $V_{th}$=threshold voltage,
- Ls=source length, and
- $\rho_s$=source resistance per unit length of doped carbon nanotube.

Compared to the CMOS-based cascode common source TIA circuit 400, the CNT-based cascode common source TIA circuit 900 shows a significant increase in DC gain and transimpedance gain, which can be attributed to large transconductance due to the number of CNTFETs. The gain of the CNT-based cascode common source TIA circuit 900 can be determined using equation (26).

$$A_{V,CNT}=g_{m,CNT}R_{out,CNT} \quad (26)$$

where
- $A_{v,CNT}$=gain of the CNT-based cascode common source TIA circuit 900,
- $g_{m,CNT}$=transconductance, and
- $R_{out}$=output resistance.

The output resistance of the CNT-based cascode common source TIA circuit 900 can be determined using equation (27).

$$R_{out,CNT}=(g_{m2,CNT}g_{d2}g_{d1})\|(g_{m3,CNT}g_{d3}g_{d4}) \quad (27)$$

where
- $R_{out,CNT}$=output resistance,
- $g_{m2,CNT}$=transconductance of the second NCNTFET 930,
- $g_{m3,CNT}$=transconductance of the first PCNTFET 935,
- $g_{d1}$=source to drain conductance of first NCNTFET 925,
- $g_{d2}$=source to drain conductance of second NCNTFET 930,
- $g_{d3}$=source to drain conductance of first PCNTFET 935, and
- $g_{d4}$=source to drain conductance of second PCNTFET 940.

The gain from node $V_{in}$ to $V_2$ can be used to determine the open loop gain of the cascode amplifier. For example, the open loop gain of the cascode amplifier may be determined using equation (28).

$$A_{V2,CNT} = \frac{V_2}{V_{in}} = \left(-\frac{1}{2}g_{m,CNT}g_d\right)^2 \quad (28)$$

where
- $A_{v2,CNT}$=gain from node $V_{in}$ to $V_2$,
- $V_2$=voltage at the output of the first stage cascode amplifier 905,
- $V_{in}$=voltage at the input terminal IN,
- $g_{m,CNT}$=transconductance, and
- $g_d$=source to drain conductance.

The source follower gain can be used determine the gain from $V_{in}$ to $V_{out}$. For example, the source follower gain can be determined using equation (29).

$$A_{V3,CNT} = \frac{V_{out}}{V_2} \approx 1 \quad (29)$$

where
- $A_{V3,CNT}$=gain from node $V_{out}$ to $V_2$,
- $V_{out}$=voltage at the output terminal OUT, and
- $V_2$=voltage at the output of the first stage cascode amplifier 905.

By substituting equations (28) and (29), the open loop gain of the CNT-based cascode common source TIA circuit 900 becomes equation (30).

$$A_{V,CNT} = A_{V2,CNT} \cdot A_{V3,CNT} = \frac{V_{out}}{V_{in}} = \left(-\frac{1}{2}g_{m,CNT}g_d\right)^2 \quad (30)$$

where
- $A_{v,CNT}$=gain of the CNT-based cascode common source TIA circuit 900,
- $A_{v2,CNT}$=gain from node $V_{in}$ to $V_2$,
- $A_{V3,CNT}$=gain from node \$T_{om}$ to $V_2$,
- $V_{out}$=voltage at the output terminal OUT,
- $V_{in}$=voltage at the input terminal IN,
- $g_{m,CNT}$=transconductance, and
- $g_d$=source to drain conductance.

The transimpedance gain of the CNT-based cascode common source TIA circuit 900 is the ratio of output voltage to input current. The transimpedance gain of the CNT-based cascode common source TIA circuit 900 can be determined, for example, using equation (31). In some embodiments, the intrinsic capacitance of the CNTFET is very small and may be neglected in a small signal analysis.

$$Z_{T,CNT} = \frac{V_{out}}{V_{in}} = \frac{R_f A_{V,CNT}}{A_{V,CNT}+1} = \frac{R_f\left(1-\frac{1}{2}g_{m,CNT}g_d\right)^2}{\left(-\frac{1}{2}g_{m,CNT}g_d\right)^2+1} \quad (31)$$

where
- $V_{out}$=voltage at the output terminal OUT,
- $I_{in}$=current at the input terminal IN,
- $R_f$=feedback resistance,
- $g_{m,CNT}$=transconductance, and
- $g_d$=source to drain conductance.

The performance of the CNT-based cascode common source TIA circuit 900 improves by optimizing the carbon nanotube diameter. The diameter of the carbon nanotube increases with increases in DC gain initially. However, further increases in carbon nanotube diameter reduces the output resistance due to increases in scattering effects, and hence DC gain deteriorates gradually. The increase in carbon nanotube diameter initially increases power dissipation significantly. Additionally, the average power dissipation increase in the CNT-based cascode common source TIA circuit 900 with carbon nanotube diameter is smaller when compared to the CMOS-based cascode common source TIA circuit 400, due to 1D ballistic transport, reduced parasitic capacitance, and the low slew rate in this device.

The performance of the CNT-based cascode common source TIA circuit 900 increases with increases in inter-nanotube spacing pitch (S). An increase in inter-nanotube spacing pitch significantly improves gain and then saturates due to increase in transconductance. However, as inter-nanotube spacing pitch increases continuously, due to large width between carbon nanotubes parasitic and screening effect leads to gain saturation.

Figure 11:
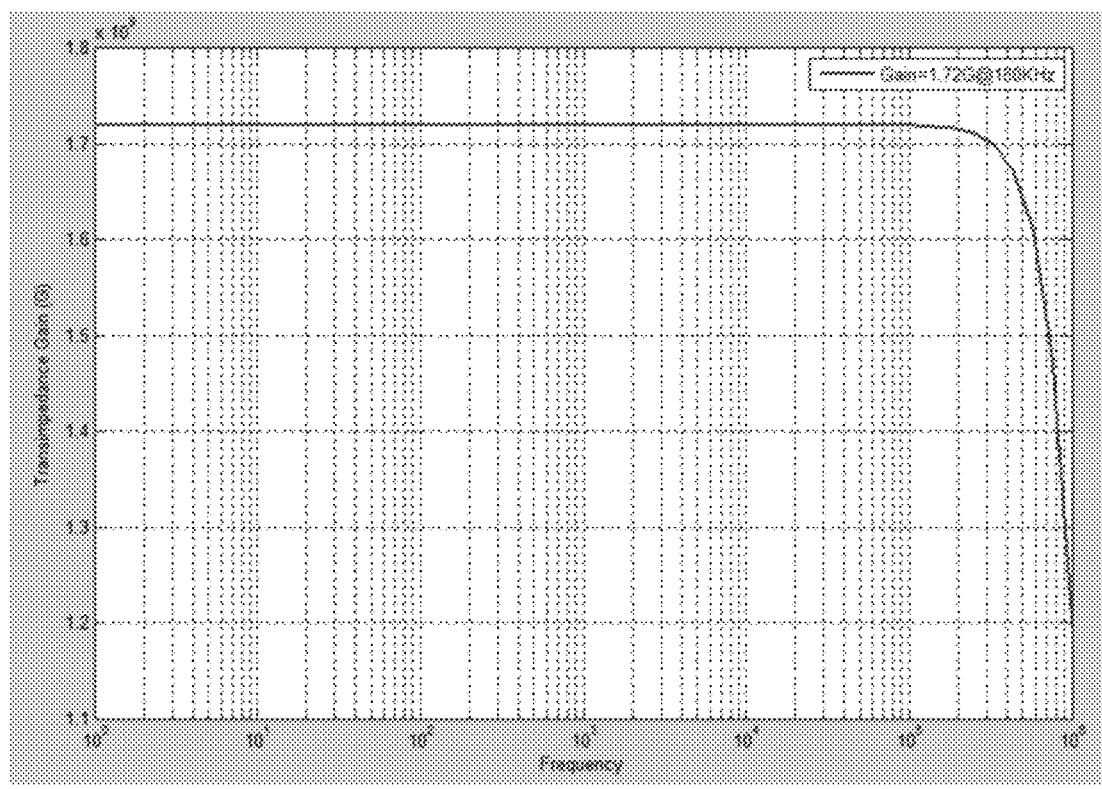
FIG. 11 is a graph of the transimpedance gain of the CMOS-based cascode common source transimpedance amplifier circuit and the biasing circuit included in FIG. 6.
Figure 12:
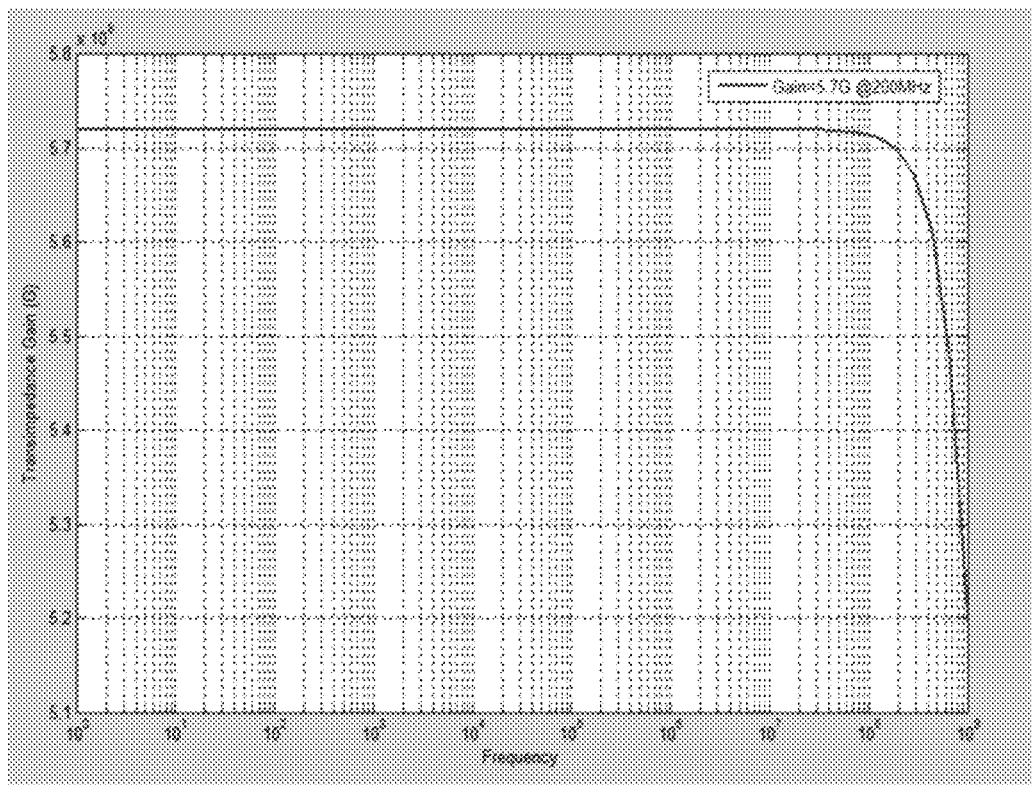
FIG. 12 is a graph of the transimpedance gain of the CNT-based cascode common source transimpedance amplifier circuit and the biasing circuit included in FIG. 10.
Figure 13:
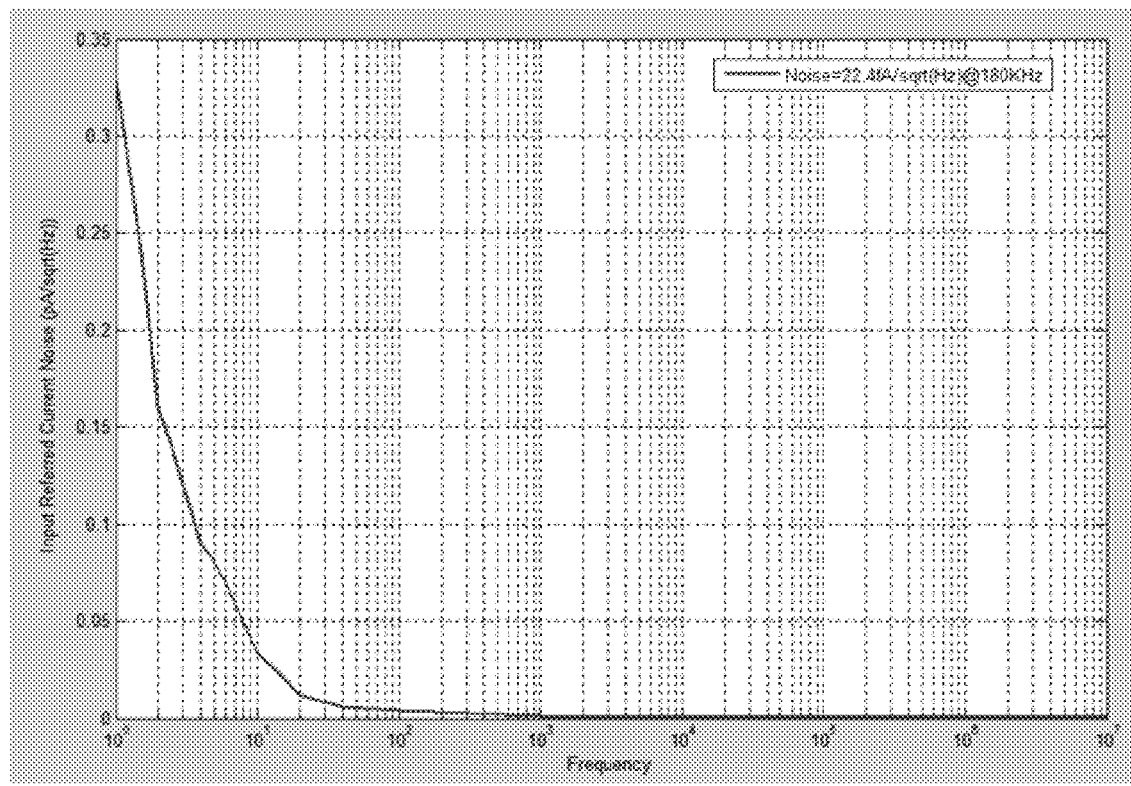
FIG. 13 is a graph of the input noise of the CMOS-based cascode common source transimpedance amplifier circuit and the biasing circuit included in FIG. 6.
Figure 14:
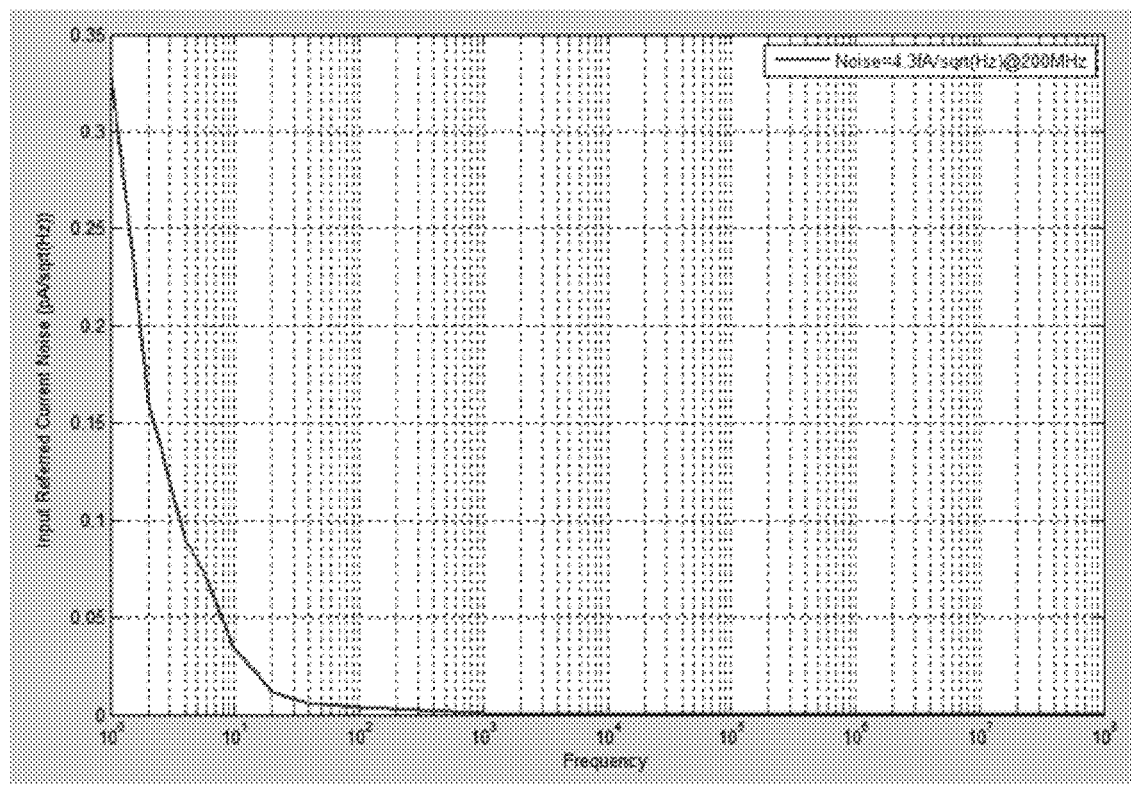
FIG. 14 is a graph of the input noise of the CNT-based cascode common source transimpedance amplifier circuit and the biasing circuit included in FIG. 10.

The transimpedance gain of the CMOS-based cascode common source TIA circuit 400 is 1.72 gigaohms with a bandwidth of 180 kilohertz, as illustrated in FIG. 11. The transimpedance gain of the CNT-based cascode common source TIA circuit 900 is 5.7 gigaohms with a bandwidth of 200 megahertz, as illustrated in FIG. 12. The input referred noise current of the CMOS-based cascode common source TIA circuit 400 is 22.4 fA/√Hz at 180 kilohertz, as illustrated in FIG. 13. The input referred noise current of the CNT-based cascode common source TIA circuit 900 is 4.3 fA/√Hz at 200 megahertz, as illustrated in FIG. 14. In some embodiments, the CMOS-based cascode common source TIA circuit 400 consumes 45.7 microwatts of power from a supply voltage of 1.4 volts. In some embodiments, the CNT-based cascode common source TIA circuit 900 consumes 6.3 picowatts of power from a supply voltage of 1.8 volts.

Table #1 illustrates a performance comparison of three conventional CMOS-based TIAs, the CMOS-based cascode common source TIA circuit 400, and the CNT-based cascode common source TIA circuit 900. As illustrated in Table #1, the CMOS-based cascode common source TIA circuit 400 and the CNT-based cascode common source TIA circuit 900 have low noise, better gain, and dissipate less power.

TABLE #1

Performance Comparison of TIAs

| Design | Input Current | Transimpedance Gain | Bandwidth | Power Consumption | Supply Voltage | Referred Noise Current |
|---|---|---|---|---|---|---|
| Conventional CMOS-based TIA | 50 μA | 215 MΩ | 615 KHz | 139 μW | 1.8 V | 910 fA/√Hz |
| Conventional CMOS-based TIA | 1 uA | 150 KΩ | 100 Hz | 90 μW | 1.8 V | 1.8 pA/√Hz |
| Conventional CMOS-based TIA | 73 uA | 100 MΩ | 1 MHz | 132 μW | 1.8 V | 158 fA/√Hz |
| CMOS-based Cascode Common Source TIA | 200 pA | 1.72 GΩ | 180 KHz | 45.7 μW | 1.4 V | 22.4 fA/√Hz |
| CNT-based Cascode Common Source TIA | 200 pA | 5.7 GΩ | 200 MHz | 6.3 pW | 1.8 V | 4.3 fA/√Hz |

Various embodiments and features are set forth in the following claims.

What is claimed is:

1. A biosensor, comprising:
    a cascode common source transimpedance amplifier circuit comprising:
        an input terminal for receiving an electrical current generated by an electrochemical reaction of an analyte on a test strip;
        a first stage comprising:
            a first n-type channel carbon nanotube field effect transistor (NCNTFET) having a gate electrode coupled to the input terminal,
            a second NCNTFET cascode connected to the first NCNTFET,
            a first p-type channel carbon nanotube field effect transistor (PCNTFET) connected to the second NCNTFET,
            a second PCNTFET cascode connected to the first PCNTFET;
        a second stage comprising:
            a third NCNTFET connected to an output of the first stage, and
            a fourth NCNTFET cascode connected to the third NCNTFET;
        an output terminal connected to an output of the second stage; and
        a biasing circuit comprising:
            a third PCNTFET having a gate electrode connected to the gate electrode of the second PCNTFET, and having a source electrode connected the reference voltage terminal,
            a fourth PCNTFET connected to the third PCNTFET, the fourth PCNTFET having a gate electrode connected to the gate electrode of the second PCNTFET and the gate electrode of the third PCNTFET, and having a source electrode connected the reference voltage terminal, wherein the third PCNTFET and the fourth PCNTFET generate a bias voltage for the second PCNTFET,
            a fifth PCNTFET connected to the fourth PCNTFET, and having a gate electrode connected to a gate electrode of the first PCNTFET, wherein the fifth PCNTFET generates a bias voltage for the first PCNTFET,
            a fifth NCNTFET connected to the fifth PCNTFET and having a gate electrode connected to a gate electrode of the second NCNTFET, wherein the fifth NCNTFET generates a bias voltage for the second NCNTFET,
            a sixth NCNTFET connected to the fifth NCNTFET and having a gate electrode connected to a gate electrode of the fourth NCNTFET, and
            a seventh NCNTFET connected to the sixth NCNTFET and the third PCNTFET, and having a gate electrode connected to a gate electrode of the fourth NCNTFET, wherein the sixth NCNTFET and the seventh NCNTFET generate a bias voltage for the fourth NCNTFET;

the cascode common source transimpedance amplifier circuit configured to convert the electrical current to an analog voltage signal;

an analog to digital converter configured to convert the analog voltage signal to a digital voltage signal; and an output circuit configured to transmit a signal indicating a measured level of the analyte based on the digital voltage signal.

2. The biosensor of claim 1, wherein a transimpedance gain of the cascode common source transimpedance amplifier circuit is 5.7 gigaohms at a bandwidth of 200 megahertz.

3. The biosensor of claim 1, wherein the cascode common source transimpedance amplifier circuit is connected to a power supply voltage source of 1.8 volts.

4. The biosensor of claim 3, wherein the cascode common source transimpedance amplifier circuit is configured to consume 6.3 picowatts of power from the power supply voltage source.

5. The biosensor of claim 1,
wherein a source electrode of the first NCNTFET is connected to a reference voltage terminal, wherein a drain electrode of the first NCNTFET is connected to a source electrode of the second NCNTFET,
wherein a drain electrode of the second NCNTFET is connected to a drain electrode of the first PCNTFET,
wherein a source electrode of the first PCNTFET is connected to a drain electrode of the second PCNTFET,
wherein a source electrode of the second PCNTFET is connected to a power supply voltage source terminal,
wherein a gate electrode of the third NCNTFET is connected to the drain electrode of the second NCNTFET and to the drain electrode of the first PCNTFET,
wherein a drain electrode of the third NCNTFET is connected to the power supply voltage source terminal,
wherein a source electrode of the third NCNTFET is connected to a drain electrode of the fourth NCNTFET,
wherein a source electrode of the fourth NCNTFET is connected to the reference voltage terminal, and
wherein the output terminal is connected to the source electrode of the third NCNTFET and to the drain electrode of the fourth NCNTFET.

6. The biosensor of claim 1, wherein the cascode common source transimpedance amplifier circuit further comprises:
a resistor connected in series between the output terminal and the input terminal, and
a capacitor connected in series between the output terminal and the input terminal.

7. The biosensor of claim 5, wherein the source electrode of the first NCNTFET is directly connected to the reference voltage terminal, and the source electrode of the fourth NCNTFET is directly connected to the reference voltage terminal.

8. A cascode common source transimpedance amplifier circuit comprising:
an input terminal for receiving an electrical current; and
a first stage comprising:
a first n-type channel field effect transistor having a gate electrode connected to the input terminal,
a second n-type channel field effect transistor cascode connected to the first n-type channel transistor,
a first p-type channel field effect transistor connected to the second n-type channel transistor, and
a second p-type channel field effect transistor cascode connected to the first p-type channel transistor;

a second stage comprising:
a third n-type channel field effect transistor connected to an output of the first stage, and
a fourth n-type channel field effect transistor cascode connected to the third n-type channel field effect transistor, and an output terminal connected to an output of the second stage, the output terminal being directly connected to the third n-type channel transistor and the fourth n-type channel transistor; and
a biasing circuit comprising:
a third p-channel field effect transistor having a gate electrode connected to the gate electrode of the second p-channel field effect transistor, and having a source electrode connected the reference voltage terminal,
a fourth p-channel field effect transistor connected to the third p-channel field effect transistor, the fourth p-channel field effect transistor having a gate electrode connected to the gate electrode of the second p-channel field effect transistor and the gate electrode of the third p-channel field effect transistor, and having a source electrode connected the reference voltage terminal, wherein the third p-channel field effect transistor and the fourth p-channel field effect transistor generate a bias voltage for the second p-channel field effect transistor,
a fifth p-channel field effect transistor connected to the fourth p-channel field effect transistor, and having a gate electrode connected to a gate electrode of the first p-channel field effect transistor, wherein the third p-channel field effect transistor generates a bias voltage for the first p-channel field effect transistor,
a fifth n-channel field effect transistor connected to the fifth p-channel field effect transistor and having a gate electrode connected to a gate electrode of the second n-channel field effect transistor, wherein the fifth n-channel field effect transistor generates a bias voltage for the second n-channel field effect transistor,
a sixth n-channel field effect transistor connected to the fifth n-channel field effect transistor and having a gate electrode connected to a gate electrode of the fourth n-channel field effect transistor, and
a seventh n-channel field effect transistor connected to the sixth n-channel field effect transistor and the third p-channel field effect transistor, and having a gate electrode connected to a gate electrode of the fourth n-channel field effect transistor, wherein the sixth n-channel field effect transistor and the seventh n-channel field effect transistor generate a bias voltage for the fourth n-channel field effect transistor; and
the cascode common source transimpedance amplifier circuit is configured to convert the electrical current to an analog voltage signal.

9. The cascode common source transimpedance amplifier circuit of claim 8, wherein the first n-type channel field effect transistor is an n-type channel metal oxide semiconductor (NMOS) transistor.

10. The cascode common source transimpedance amplifier circuit of claim 8, wherein the first n-type channel field effect transistor is an n-type channel carbon nanotube field effect transistor (NCNTFET).

11. The cascode common source transimpedance amplifier circuit of claim 8, further comprising:
a resistor connected in series between the output terminal and the input terminal, and a capacitor connected in series between the output terminal and the input terminal.

12. The cascode common source transimpedance amplifier circuit of claim 8, wherein a source electrode of the first n-channel field effect transistor is directly connected to a reference voltage terminal, and a source electrode of the fourth n-channel field effect transistor is directly connected to the reference voltage terminal.

13. A biosensor comprising:
a cascode common source transimpedance amplifier circuit comprising:
   an input terminal configured to receive an electrical current generated by an electrochemical reaction of an analyte on a test strip;
   a first stage;
   a second stage comprising:
      a first NMOS transistor connected to an output of the first stage, and
      a second NMOS transistor cascode connected to the first NMOS transistor;
   a biasing circuit comprising:
      a first PMOS transistor having a source electrode connected the reference voltage terminal;
      a second PMOS transistor connected to the first PMOS transistor, and having a source electrode connected the reference voltage terminal, wherein the first PMOS transistor and the second PMOS transistor generate a first bias voltage for the first stage;
      a third PMOS transistor connected to the second PMOS transistor, wherein the third PMOS transistor generates a second bias voltage for the first stage;
      a third NMOS transistor connected to the third PMOS transistor, wherein the third NMOS transistor generates a third bias voltage for the first stage;
      a fourth NMOS transistor connected to the third NMOS transistor and having a gate electrode connected to a gate electrode of the second NMOS transistor; and
      a fifth NMOS transistor connected to the fourth NMOS transistor and the first PMOS transistor, and having a gate electrode connected to a gate electrode of the second NMOS transistor, wherein the fourth NMOS transistor and the fifth NMOS transistor generate a bias voltage for the second NMOS transistor; and
   an output terminal connected to an output of the second stage, the output terminal being directly connected to the first NMOS transistor and the second NMOS transistor,
   wherein the cascode common source transimpedance amplifier circuit is configured to convert the electrical current to an analog voltage signal;
an analog to digital converter configured to convert the analog voltage signal to a digital voltage signal; and
an output circuit configured to transmit a signal indicating a measured level of the analyte based on the digital voltage signal.

14. The biosensor of claim 13, wherein the cascode common source transimpedance amplifier circuit further includes
   a resistor connected in series between the output terminal and the input terminal, and
   a capacitor connected in series between the output terminal and the input terminal.

15. The biosensor of claim 13, wherein a transimpedance gain of the cascode common source transimpedance amplifier circuit is 1.72 gigaohms at a bandwidth of 180 kilohertz.

16. The biosensor of claim 13, wherein the cascode common source transimpedance amplifier circuit is connected to a power supply voltage source of 1.4 volts.

17. The biosensor of claim 16, wherein the cascode common source transimpedance amplifier circuit is configured to consume 45.7 microwatts of power from the power supply voltage source.

* * * * *